United States Patent
Mao et al.

(10) Patent No.: US 10,774,094 B2
(45) Date of Patent: Sep. 15, 2020

(54) CRYSTAL FORMS AND SALT FORMS OF 7H-PYRROLO[2,3-D]PYRIMIDINE COMPOUNDS AND PREPARATION METHOD THEREOF

(71) Applicant: Wuxi Fortune Pharmaceutical Co., Ltd, Wuxi, Jiangsu (CN)

(72) Inventors: Weiwei Mao, Jiangsu (CN); Hao Wu, Jiangsu (CN); Qiang Guo, Jiangsu (CN); Xuejian Zheng, Jiangsu (CN); Yonggang Liao, Jiansu (CN)

(73) Assignee: Wuxi Fortune Pharmaceutical Co., Ltd, Wuxi (CN)

(*) Notice: Subject to any disclaimer, the term of this patent is extended or adjusted under 35 U.S.C. 154(b) by 0 days.

(21) Appl. No.: 16/336,361

(22) PCT Filed: Nov. 23, 2017

(86) PCT No.: PCT/CN2017/112493
§ 371 (c)(1),
(2) Date: Mar. 25, 2019

(87) PCT Pub. No.: WO2018/095345
PCT Pub. Date: May 31, 2018

(65) Prior Publication Data
US 2019/0218231 A1    Jul. 18, 2019

(30) Foreign Application Priority Data
Nov. 23, 2016   (CN) .......................... 2016 1 1046683

(51) Int. Cl.
| | | |
|---|---|---|
| *C07D 519/00* | (2006.01) |
| *A61K 31/519* | (2006.01) |
| *A61K 31/437* | (2006.01) |
| *A61P 19/02* | (2006.01) |
| *A61P 29/00* | (2006.01) |

(52) U.S. Cl.
CPC .......... *C07D 519/00* (2013.01); *A61K 31/437* (2013.01); *A61K 31/519* (2013.01); *A61P 19/02* (2018.01); *A61P 29/00* (2018.01); *C07B 2200/07* (2013.01); *C07B 2200/13* (2013.01)

(58) Field of Classification Search
CPC .......................... C07B 2200/13; C07D 519/00
See application file for complete search history.

(56) References Cited

U.S. PATENT DOCUMENTS

| | | | |
|---|---|---|---|
| 9,617,258 B2 | 4/2017 | Thorarensen et al. |
| 2018/0162879 A1 | 6/2018 | Wu et al. |

FOREIGN PATENT DOCUMENTS

| | | |
|---|---|---|
| CN | 107531711 | 1/2018 |
| TW | 201524977 | 7/2015 |
| WO | WO0142246 A2 | 6/2001 |

OTHER PUBLICATIONS

Bhattacharya et al. (Brittain, ed. Polymorphism in Pharmaceutical Solids, 2009, p. 334.*
Paulekuhn et al. (J. Med. Chem., 2007, 50, pp. 6665-6672).*
Berge (Journal of Pharmaceutical Sciences, 1977, 66(1), pp. 1-19).*
Caira, Crystalline Polymorphism of Organic Compounds, Topics in Current Chemistry, 1998, pp. 163-208, vol. 198, Springer, Berlin, ISSN 0340-1022.
Extended European Search Report, Application No. EP17873546, dated Jul. 12, 2019, Munich.
Australian Examination Report No. 1, Application No. AU2017366375, dated Sep. 11, 2019.

* cited by examiner

*Primary Examiner* — Susanna Moore
(74) *Attorney, Agent, or Firm* — Dinsmore & Shohl LLP; Julie K. Staple

(57) ABSTRACT

The present invention discloses crystal forms and salt forms of a 7H-pyrrolo[2,3-d]pyrimidine compounds and preparation methods thereof, and further discloses use of the crystal forms and the salt forms in the manufacture of a medicament for treating arthritis.

10 Claims, 18 Drawing Sheets

CRYSTAL FORMS AND SALT FORMS OF 7H-PYRROLO[2,3-D]PYRIMIDINE COMPOUNDS AND PREPARATION METHOD THEREOF

FIELD OF THE INVENTION

The present invention relates to crystal forms and salt forms of 7H-pyrrolo[2,3-d]pyrimidine compounds and preparation method thereof, and also relates to use of the crystal form and the salt form in the manufacture of a medicament for treating arthritis.

BACKGROUND OF THE INVENTION

JAK belongs to the family of tyrosine kinases involved in inflammation, autoimmune diseases, proliferative diseases, transplant rejection, impaired cartilage turnover-related diseases, congenital cartilage malformations, and/or diseases associated with excessive secretion of IL6. The present invention also provides a method for preparing the compound or a pharmaceutical composition comprising the compound, and a method for preventing and/or treating inflammation, autoimmune diseases, proliferative diseases, transplant rejection, impaired cartilage turnover-related diseases, congenital cartilage malformations, and/or diseases associated with excessive secretion of IL6 by administrating the compound of the present invention.

Janus kinase (JAK) is a cytoplasmic tyrosine kinase that transduces a cytokine signal from a membrane receptor to an STAT transcription factor. The prior art has described four members of the JAK family: JAK1, JAK2, JAK3 and TYK2. When cytokines bind to their receptors, JAK family members are auto-phosphorylated and/or trans-phosphorylated from each other, followed by STATs phosphorylation, and then are migrated into the cell nucleus to regulate the transcription. JAK-STAT intracellular signal transduction is suitable for interferons, most interleukins, as well as various cytokines and endocrine factors, such as EPO, TPO, GH, OSM, LIF, CNTF, GM-CSF and PRL (Vainchenker W. et al. (2008)).

A combinatorial study of a genetic model and a small molecule JAK inhibitor has revealed the therapeutic potential of several JAKs. It has been confirmed by mouse and human genetics that JAK3 is an immunosuppressive target (O'Shea J. et al. (2004)). A JAK3 inhibitor has been successfully used in clinical development. At first, it was used in organ transplant rejection, and later also used in other immunoinflammatory indications such as rheumatoid arthritis (RA), psoriasis and Crohn's disease (http://clinicaltrials.gov/). It has been confirmed by human genetics and mouse knockout studies that TYK2 is a potential target for immunoinflammatory diseases (Levy D. and Loomis C. (2007)). JAK1 is a new target in the field of immunoinflammatory diseases. The heterodimerization of JAK1 and other JAKs arouses a transduction of cytokine-driven pro-inflammatory signaling. Thus, it is expected that inhibition of JAK1 and/or other JAKs has a therapeutic benefit for a series of inflammatory diseases and other diseases driven by JAK-mediated signal transduction.

SUMMARY OF THE INVENTION

The present invention provides a crystal form A of the following compound 1, of which the X-ray powder diffraction pattern has characteristic diffraction peaks at the following 2θ angles: 12.38±0.2°, 13.34±0.2° and 22.09±0.2°.

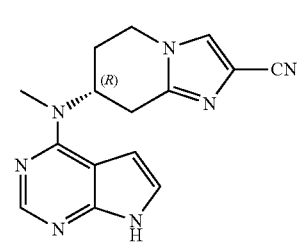

Compound 1

In some embodiments of the present invention, the X-ray powder diffraction pattern of the crystal form A of the compound 1 has characteristic diffraction peaks at the following 2θ angles: 12.38±0.2°, 13.34±0.2°, 15.85±0.2°, 22.09±0.2°, 23.71±0.2°, 25.38±0.2°, 26.21±0.2° and 26.81±0.2°.

In some embodiments of the present invention, the X-ray powder diffraction (XRPD) pattern of the crystal form A of the compound 1 is as shown in FIG. 1.

In some embodiments of the present invention, the analytic data of the XRPD pattern of the crystal form A of the compound 1 are shown in Table 1.

TABLE 1

Analytic Data of XRPD Pattern of Crystal Form A of Compound 1

| NO. | 2θ angle (°) | Interplanar distance (Å) | Relative intensity (%) |
|---|---|---|---|
| 1 | 12.383 | 7.142 | 77.4 |
| 2 | 13.345 | 6.6293 | 68 |
| 3 | 14.808 | 5.9773 | 2.3 |
| 4 | 15.854 | 5.5852 | 61.2 |
| 5 | 19.345 | 4.5846 | 10.3 |
| 6 | 21.516 | 4.1267 | 10.9 |
| 7 | 22.087 | 4.0212 | 100 |
| 8 | 23.39 | 3.8 | 2.5 |
| 9 | 23.706 | 3.7501 | 62.4 |
| 10 | 25.383 | 3.506 | 23.5 |
| 11 | 26.209 | 3.3974 | 29.7 |
| 12 | 26.806 | 3.323 | 25.4 |
| 13 | 29.056 | 3.0706 | 2.9 |
| 14 | 29.352 | 3.0403 | 4.7 |
| 15 | 31.968 | 2.7973 | 1.3 |
| 16 | 33.094 | 2.7046 | 5.4 |
| 17 | 33.473 | 2.6749 | 4.9 |
| 18 | 34.598 | 2.5904 | 4.4 |
| 19 | 36.412 | 2.4654 | 2.1 |
| 20 | 37.669 | 2.386 | 4.9 |
| 21 | 38.008 | 2.3655 | 2.6 |
| 22 | 38.835 | 2.317 | 1.3 |
| 23 | 39.015 | 2.3067 | 2.9 |

In some embodiments of the present invention, the differential scanning calorimetry (DSC) curve of the crystal form A of the compound 1 has an endothermic peak at 314.89° C.±2° C.

In some embodiments of the present invention, the DSC pattern of the crystal form A of the compound 1 is as shown in FIG. 2.

In some embodiments of the present invention, the weight loss of the thermogravimetric analysis (TGA) curve of the crystal form A of the compound 1 is up to 0.2516±0.2% at 120.00±2° C.

In some embodiments of the present invention, the TGA pattern of the crystal form A of the compound 1 is as shown in FIG. 3.

The present invention further provides a crystal form B of the compound 1, of which the X-ray powder diffraction pattern has characteristic diffraction peaks at the following 2θ angles: 12.25±0.2°, 21.97±0.2° and 23.62±0.2°.

In some embodiments of the present invention, the X-ray powder diffraction pattern of the crystal form B of the compound 1 has characteristic diffraction peaks at the following 2θ angles: 12.25±0.2°, 13.24±0.2°, 15.77±0.2°, 21.97±0.2°, 23.62±0.2°, 25.24±0.2°, 26.70±0.2° and 37.51±0.2°.

In some embodiments of the present invention, the XRPD pattern of the crystal form B of the compound 1 is as shown in FIG. 4.

In some embodiments of the present invention, the analytic data of the XRPD pattern of the crystal form B of the compound 1 are shown in Table 2.

TABLE 2

Analytic Data of XRPD Pattern of Crystal Form B of Compound 1

| NO. | 2θ angle (°) | Interplanar distance (Å) | Relative intensity (%) |
|---|---|---|---|
| 1 | 10.798 | 8.1866 | 1.5 |
| 2 | 12.254 | 7.2171 | 100 |
| 3 | 13.245 | 6.6793 | 11.4 |
| 4 | 14.445 | 6.1268 | 2.3 |
| 5 | 15.774 | 5.6133 | 4.4 |
| 6 | 21.376 | 4.1533 | 4.2 |
| 7 | 21.966 | 4.0431 | 15.7 |
| 8 | 23.623 | 3.7631 | 19.8 |
| 9 | 24.731 | 3.5969 | 1.4 |
| 10 | 25.241 | 3.5254 | 4.1 |
| 11 | 26.073 | 3.4148 | 0.8 |
| 12 | 26.705 | 3.3353 | 8.4 |
| 13 | 29.384 | 3.0371 | 0.8 |
| 14 | 32.956 | 2.7156 | 3.6 |
| 15 | 33.33 | 2.686 | 0.7 |
| 16 | 34.531 | 2.5953 | 0.9 |
| 17 | 35.205 | 2.5471 | 0.3 |
| 18 | 37.511 | 2.3956 | 18 |
| 19 | 37.606 | 2.3899 | 9 |
| 20 | 37.865 | 2.3741 | 1.7 |
| 21 | 38.904 | 2.3131 | 0.9 |

In some embodiments of the present invention, the differential scanning calorimetry curve of the crystal form B of the compound 1 has an endothermic peak at 322.33° C.±2° C.

In some embodiments of the present invention, the DSC pattern of the crystal form B of the compound 1 is as shown in FIG. 5.

In some embodiments of the present invention, the weight loss of the thermogravimetric analysis curve of the crystal form B of the compound 1 is up to 0.6939±0.2% at 120±2° C.

In some embodiments of the present invention, the TGA pattern of the crystal form B of the compound 1 is as shown in FIG. 6.

The present invention further provides a crystal form C of the compound 1, of which the X-ray powder diffraction pattern has characteristic diffraction peaks at the following 2θ angles: 12.40±0.2° and 37.65±0.2°.

In some embodiments of the present invention, the X-ray powder diffraction pattern of the crystal form C of the compound 1 has characteristic diffraction peaks at the following 2θ angles: 12.40±0.2°, 13.37±0.2°, 21.51±0.2°, 22.14±0.2°, 24.87±0.2°, 25.40±0.2° and 37.65±0.2°.

In some embodiments of the present invention, the XRPD pattern of the crystal form C of the compound 1 is as shown in FIG. 7.

In some embodiments of the present invention, the analytic data of the XRPD pattern of the crystal form C of the compound 1 are shown in Table 3.

TABLE 3

Analytic Data of XRPD Pattern of Crystal Form C of Compound 1

| NO. | 2θ angle (°) | Interplanar distance (Å) | Relative intensity (%) |
|---|---|---|---|
| 1 | 12.4 | 7.1325 | 100 |
| 2 | 13.367 | 6.6183 | 1.3 |
| 3 | 21.509 | 4.1279 | 1 |
| 4 | 22.139 | 4.0118 | 9 |
| 5 | 24.871 | 3.5771 | 1.3 |
| 6 | 25.398 | 3.504 | 1.8 |
| 7 | 37.651 | 2.3871 | 16.8 |
| 8 | 37.744 | 2.3814 | 8.5 |

In some embodiments of the present invention, the differential scanning calorimetry curve of the crystal form C of the compound 1 has an endothermic peak at 326.62° C.±2° C.

In some embodiments of the present invention, the DSC pattern of the crystal form C of the compound 1 is as shown in FIG. 8.

In some embodiments of the present invention, the weight loss of the thermogravimetric analysis curve of the crystal form C of the compound 1 is up to 0.5564±0.2% at 120±2° C.

In some embodiments of the present invention, the TGA pattern of the crystal form C of the compound 1 is as shown in FIG. 9.

The present invention further provides a crystal form D of the compound 1, of which the X-ray powder diffraction pattern has characteristic diffraction peaks at the following 2θ angles: 12.36±0.2° and 37.62±0.2°.

In some embodiments of the present invention, the X-ray powder diffraction pattern of the crystal form D of the compound 1 has characteristic diffraction peaks at the following 2θ angles: 12.36±0.2°, 24.84±0.2° and 37.62±0.2°.

In some embodiments of the present invention, the XRPD pattern of the crystal form C of the compound 1 is as shown in FIG. 10.

In some embodiments of the present invention, the analytic data of the XRPD pattern of the crystal form C of the compound 1 are shown in Table 4.

TABLE 4

Analytic Data of XRPD Pattern of Crystal Form D of Compound 1

| NO. | 2θ angle (°) | Interplanar distance (Å) | Relative intensity (%) |
|---|---|---|---|
| 1 | 12.365 | 7.1522 | 100 |
| 2 | 21.512 | 4.1274 | 0.4 |
| 3 | 22.089 | 4.0208 | 0.5 |
| 4 | 24.836 | 3.582 | 1.2 |
| 5 | 37.615 | 2.3893 | 14.1 |
| 6 | 37.706 | 2.3837 | 6.9 |
| 7 | 38.023 | 2.3646 | 0.9 |

In some embodiments of the present invention, the differential scanning calorimetry curve of the crystal form D of the compound 1 has an endothermic peak at 326.13° C.±2° C.

In some embodiments of the present invention, the DSC pattern of the crystal form D of the compound 1 is as shown in FIG. 11.

In some embodiments of the present invention, the weight loss of the thermogravimetric analysis curve of the crystal form D of the compound 1 is up to 0.3076±0.3% at 185.13±2° C.

In some embodiments of the present invention, the TGA pattern of the crystal form D of the compound 1 is as shown in FIG. 12.

The present invention further provides p-toluenesulfonate of the compound 1, which is shown as the following compound 2:

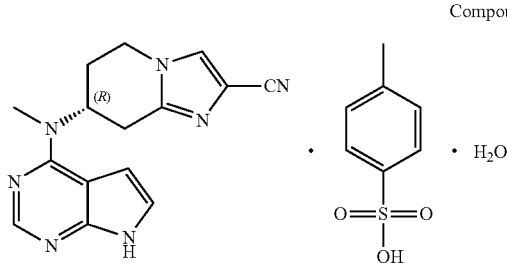

Compound 2

The present invention further provides a crystal form E of the compound 2, of which the X-ray powder diffraction pattern has characteristic diffraction peaks at the following 2θ angles: 6.21±0.2°, 10.92±0.2° and 12.78±0.2°.

In some embodiments of the present invention, the X-ray powder diffraction pattern of the crystal form E of the compound 2 has characteristic diffraction peaks at the following 2θ angles: 6.21±0.2°, 10.92±0.2°, 12.34±0.2°, 12.78±0.2°, 15.16±0.2°, 20.23±0.2°, 22.77±0.2° and 23.03±0.2°.

In some embodiments of the present invention, the XRPD pattern of the crystal form E of the compound 2 is as shown in FIG. 13.

In some embodiments of the present invention, the analytic data of the XRPD pattern of the crystal form E of the compound 2 are shown in Table 5.

TABLE 5

Analytic Data of XRPD Pattern of Crystal Form E of Compound 2

| NO. | 2θ angle (°) | Interplanar distance (Å) | Relative intensity (%) |
|---|---|---|---|
| 1 | 6.21 | 14.2216 | 71.7 |
| 2 | 7.594 | 11.632 | 1.6 |
| 3 | 10.919 | 8.0958 | 61.8 |
| 4 | 12.343 | 7.1651 | 20.1 |
| 5 | 12.776 | 6.9233 | 100 |
| 6 | 14.882 | 5.9477 | 5.8 |
| 7 | 15.16 | 5.8394 | 17.5 |
| 8 | 15.656 | 5.6556 | 3.6 |
| 9 | 16.11 | 5.4972 | 15 |
| 10 | 17.015 | 5.2067 | 1.7 |
| 11 | 17.509 | 5.0609 | 9.2 |
| 12 | 17.728 | 4.999 | 12.8 |
| 13 | 18.18 | 4.8758 | 12.8 |
| 14 | 18.513 | 4.7887 | 4.3 |
| 15 | 20.231 | 4.3858 | 28 |
| 16 | 20.447 | 4.3399 | 14.9 |
| 17 | 20.805 | 4.2661 | 2.5 |
| 18 | 21.081 | 4.2108 | 2.7 |
| 19 | 21.825 | 4.0689 | 5.9 |
| 20 | 22.458 | 3.9557 | 3.9 |
| 21 | 22.774 | 3.9014 | 39.4 |
| 22 | 23.033 | 3.8581 | 38.5 |
| 23 | 23.983 | 3.7075 | 3.4 |
| 24 | 25.003 | 3.5585 | 3.3 |
| 25 | 25.559 | 3.4822 | 3 |
| 26 | 25.831 | 3.4463 | 8.9 |
| 27 | 26.797 | 3.3241 | 9.4 |
| 28 | 27.506 | 3.24 | 2.7 |
| 29 | 27.718 | 3.2158 | 3.8 |

TABLE 5-continued

Analytic Data of XRPD Pattern of Crystal Form E of Compound 2

| NO. | 2θ angle (°) | Interplanar distance (Å) | Relative intensity (%) |
|---|---|---|---|
| 30 | 28.216 | 3.1602 | 5.5 |
| 31 | 29.068 | 3.0694 | 4.5 |
| 32 | 29.522 | 3.0232 | 12.8 |
| 33 | 29.914 | 2.9845 | 23 |
| 34 | 30.448 | 2.9333 | 5.3 |
| 35 | 31.001 | 2.8823 | 8.5 |
| 36 | 32.259 | 2.7727 | 2.7 |
| 37 | 32.951 | 2.716 | 2.1 |
| 38 | 34.019 | 2.6332 | 3.3 |
| 39 | 37.408 | 2.402 | 3.6 |
| 40 | 37.901 | 2.3719 | 2.5 |

In some embodiments of the present invention, the differential scanning calorimetry curve of the crystal form E of the compound 2 has initial points of endothermic peaks at 90.87±2° C., 149.18±2° C. and 207.91±2° C.

In some embodiments of the present invention, the DSC pattern of the crystal form E of the compound 2 is as shown in FIG. 14.

In some embodiments of the present invention, the weight loss of the thermogravimetric analytic curve of the crystal form E of the compound 2 reaches up to 3.723±0.5% at 64.37±2° C.

In some embodiments of the present invention, the TGA pattern of the crystal form E of the compound 2 is as shown in FIG. 15.

The present invention further provides a p-trifluoroacetate of the compound 1, which is shown as the following compound 3:

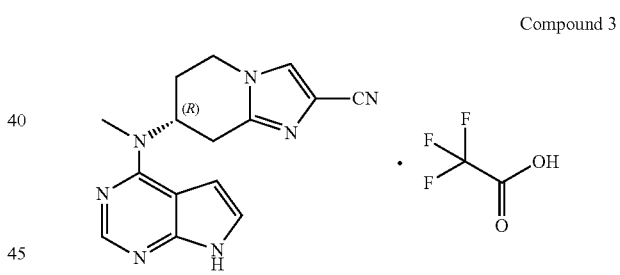

Compound 3

In some embodiments of the present invention, the X-ray powder diffraction pattern of the crystal form F of the compound 3 has characteristic diffraction peaks at the following 2θ angles: 12.89±0.2°, 18.79±0.2° and 24.70±0.2°.

In some embodiments of the present invention, the X-ray powder diffraction pattern of the crystal form F of the compound 3 has characteristic diffraction peaks at the following 2θ angles: 12.89±0.2°, 15.78±0.2°, 17.67±0.2°, 18.79±0.2°, 19.38±0.2°, 20.47±0.2°, 24.70±0.2° and 25.66±0.2°.

TABLE 6

Analytic Data of XRPD Pattern of Crystal Form F of Compound 3

| NO. | 2θ angle (°) | Interplanar distance (Å) | Relative intensity (%) |
|---|---|---|---|
| 1 | 8.541 | 10.3438 | 17.3 |
| 2 | 10.182 | 8.6804 | 5.7 |
| 3 | 12.279 | 7.2025 | 2.5 |

TABLE 6-continued

Analytic Data of XRPD Pattern of Crystal Form F of Compound 3

| NO. | 2θ angle (°) | Interplanar distance (Å) | Relative intensity (%) |
| --- | --- | --- | --- |
| 4 | 12.452 | 7.1027 | 2.6 |
| 5 | 12.887 | 6.864 | 53.4 |
| 6 | 13.479 | 6.5637 | 6.2 |
| 7 | 14.074 | 6.2875 | 12.5 |
| 8 | 15.275 | 5.7957 | 37.5 |
| 9 | 16.638 | 5.3237 | 15.7 |
| 10 | 17.095 | 5.1825 | 13.3 |
| 11 | 17.668 | 5.0158 | 44.4 |
| 12 | 18.415 | 4.814 | 31.5 |
| 13 | 18.792 | 4.7181 | 44.9 |
| 14 | 19.383 | 4.5756 | 26.4 |
| 15 | 20.47 | 4.335 | 20.9 |
| 16 | 21.141 | 4.1989 | 15.3 |
| 17 | 23.135 | 3.8414 | 6.8 |
| 18 | 24.304 | 3.6592 | 3 |
| 19 | 24.698 | 3.6017 | 100 |
| 20 | 25.663 | 3.4685 | 27.8 |
| 21 | 25.923 | 3.4343 | 8.5 |
| 22 | 26.57 | 3.352 | 3.2 |
| 23 | 27.128 | 3.2844 | 7.5 |
| 24 | 27.678 | 3.2203 | 4.7 |
| 25 | 27.996 | 3.1845 | 7.5 |
| 26 | 28.334 | 3.1473 | 1.9 |
| 27 | 28.671 | 3.111 | 3.8 |
| 28 | 29.241 | 3.0517 | 4.1 |
| 29 | 30.264 | 2.9507 | 11 |
| 30 | 30.82 | 2.8988 | 2.9 |
| 31 | 34.255 | 2.6155 | 2.5 |
| 32 | 35.539 | 2.5239 | 2.1 |
| 33 | 36.231 | 2.4773 | 2.7 |
| 34 | 37.277 | 2.4102 | 2.3 |

In some embodiments of the present invention, the XRPD pattern of the crystal form F of the compound 3 is as shown in FIG. 16.

In some embodiments of the present invention, the differential scanning calorimetry curve of the crystal form F of the compound 3 has an initial point of an endothermic peak at 203.73° C.±2° C.

In some embodiments of the present invention, the DSC pattern of the crystal form F of the compound 3 is as shown in FIG. 17.

In some embodiments of the present invention, the weight loss of the thermogravimetric analytic curve of the crystal form F of the compound 3 reaches up to 0.9086±0.2% at 138.71±2° C.

In some embodiments of the present invention, the TGA pattern of the crystal form F of the compound 3 is as shown in FIG. 18.

Technical Effect

The crystal forms A, B, C and D of the compound 1, the crystal form E of the compound 2, and the crystal form F of the compound 3 have stable properties, low hygroscopicity, excellent water solubility and promising drug-formation.

DEFINITION AND DESCRIPTION

Unless otherwise stated, the following terms and phrases used herein are intended to have the following meanings. A specific phrase or term should not be considered undefined or unclear without a special definition, but should be understood in the ordinary sense. When a trade name appears herein, it is intended to refer to its corresponding commodity or its active ingredient.

Intermediate compounds of the present invention can be prepared through a variety of synthetic methods well known to those skilled in the art, including the particular embodiments listed below, the embodiments formed by combining the above embodiments with other chemical synthesis methods, and the equivalents well known to those skilled in the art. Preferable embodiments include, but are not limited to, examples of the present invention.

The chemical reactions in embodiments of the present invention are carried out in suitable solvents which should be suitable for the chemical changes of the present invention and the reagents and materials required by the reactions. In order to obtain the compounds of the present invention, sometimes it is necessary for those skilled in the art to modify or select the synthetic steps or reaction schemes based on the existing embodiments.

The present invention will be described in detail via the following examples, which are not intended to limit the present invention in any way.

All the solvents used in the present invention are commercially available, and are directly used without further purification.

The following abbreviations are used in the present invention: DMF represents dimethylformamide; MsOH represents methanesulfonic acid; EtOH represents ethanol; and NaOH represents sodium hydroxide.

Compounds are named manually or by the ChemDraw® software, and the commercially available compounds use the name from the supplier catalogue.

The X-Ray Powder Diffractometer (XRPD) Method of the Present Invention

Instrument model: Brooke D8 advance X-ray diffractometer; and

Test method: about 10-20 mg of a sample for XRPD detection.

Detailed parameters for XRPD are as follows:

Light pipe: Cu, kα, (λ=1.54056Å);
Light pipe voltage: 40 kV; Light pipe current: 40 mA;
Divergence slit: 0.60 mm;
Detector slit: 10.50 mm;
Anti-scattering slit: 7.10 mm;
Scanning range: 4-40 deg;
Step diameter: 0.02 deg;
Step size: 0.12 seconds; and
Rotation speed of sample disc: 15 rpm.

The Differential Scanning Calorimeter (DSC) Method of the Present Invention

Instrument model: TAQ2000 differential scanning calorimeter; and

Test method: placing a sample (about 1 mg) in a DSC aluminum pot for testing, and heating the sample from 25° C. to 350° C. at a rate of 10° C./min under the condition of 50 mL/min of $N_2$.

The Thermal Gravimetric Analyzer (TGA) Method of the Present Invention

Instrument model: TAQ5000IR thermal gravimetric analyzer; and

Test method: placing a sample (2-5 mg) into a TGA platinum pot for testing, and heating the sample from room temperature to 350° C. (or to weight loss of 20%) at a rate of 10° C./min under the condition of 25 mL/min $N_2$.

DETAILED DESCRIPTION OF THE EMBODIMENTS

Figure 1:
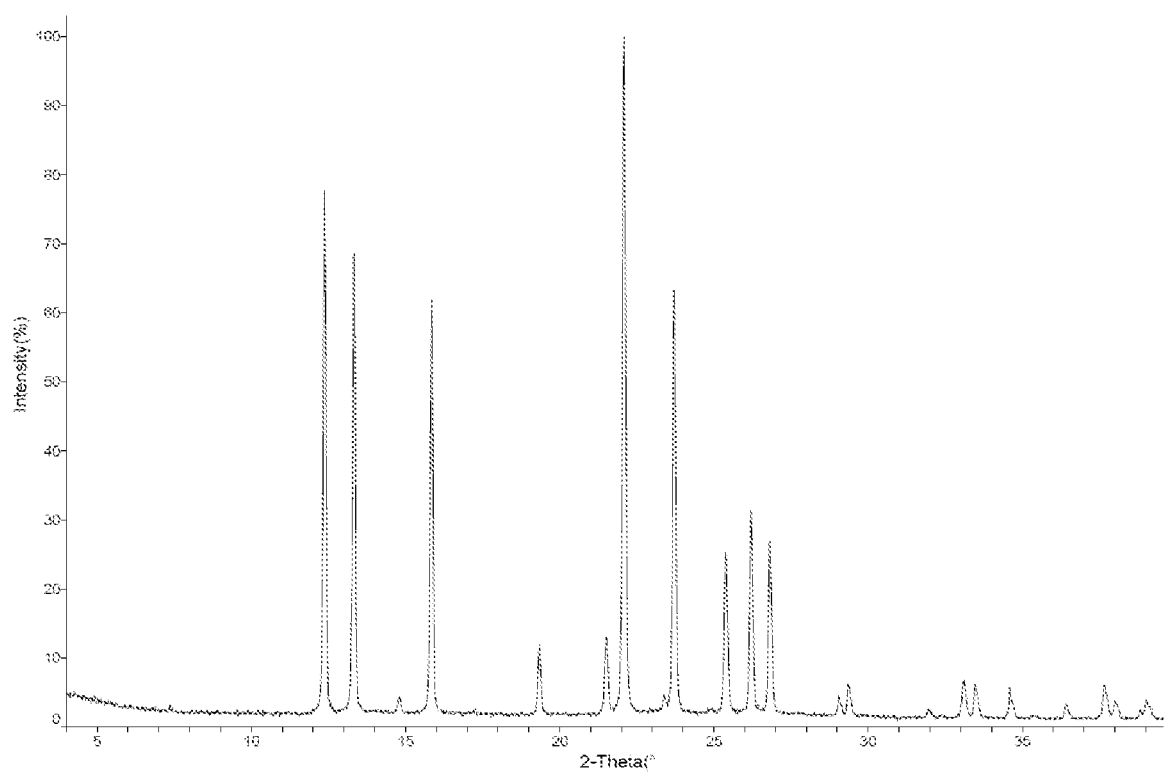
FIG. 1 is an XRPD pattern of Cu-kα radiation of the crystal form A of the compound 1.
Figure 2:
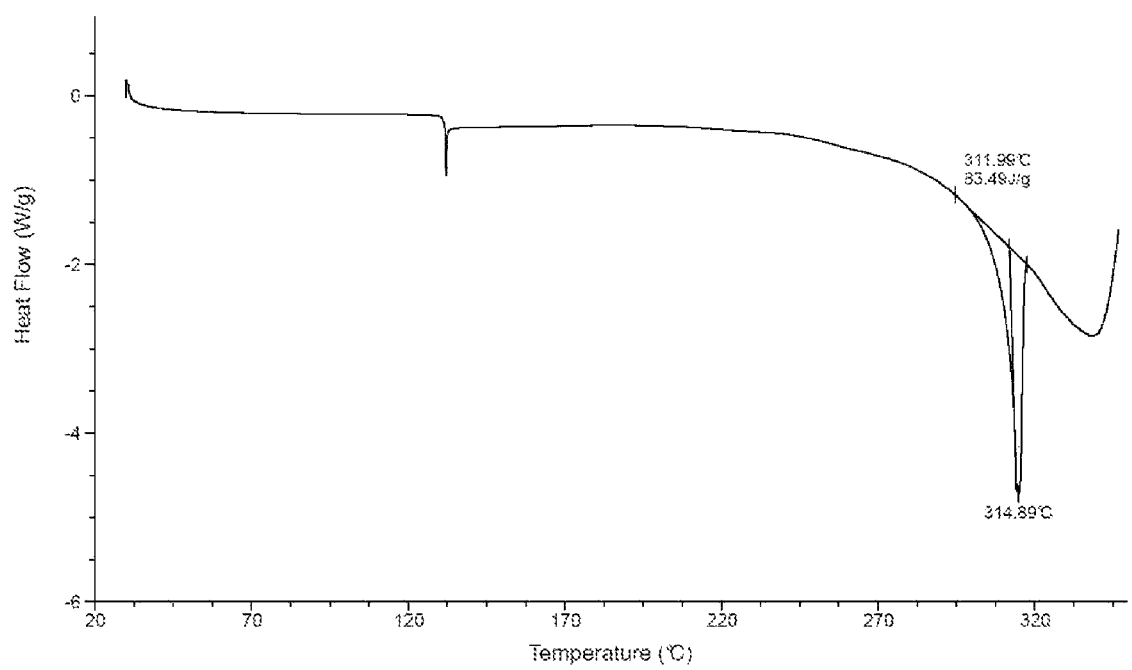
FIG. 2 is a DSC pattern of the crystal form A of the compound 1.
Figure 3:
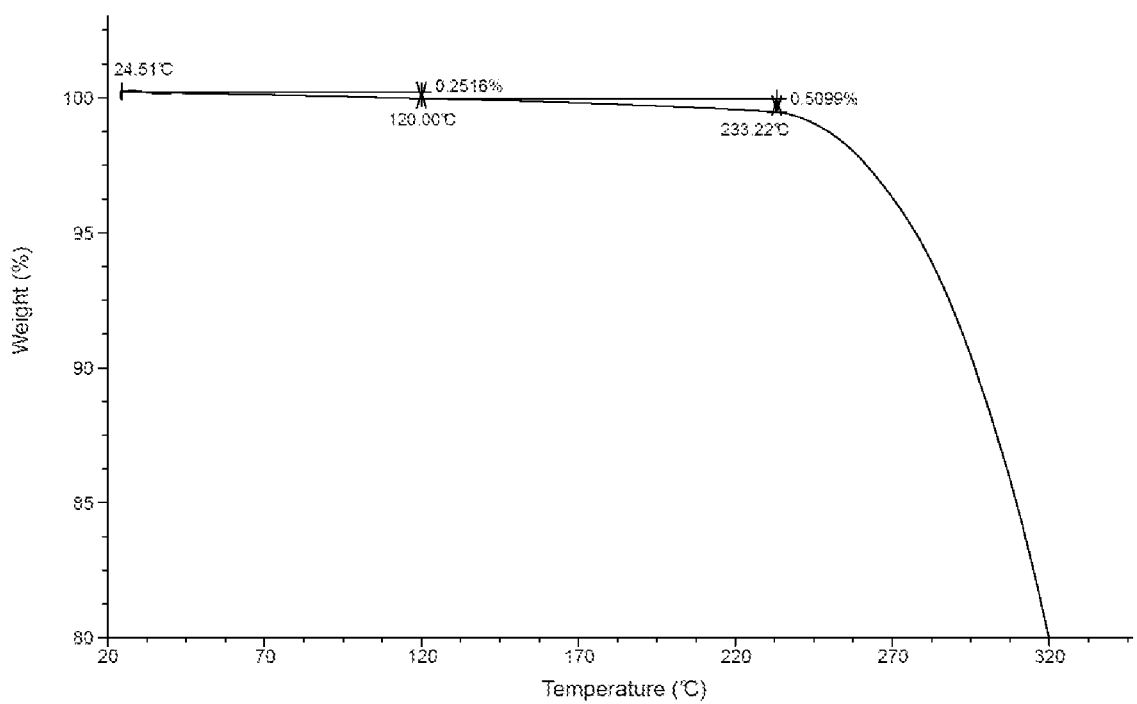
FIG. 3 is a TGA pattern of the crystal form A of the compound 1.

The present invention is further illustrated below in combination with the specific examples in order to better understand the content of the present invention, but these specific examples are not intended to limit the scope of the present invention.

Example 1: Preparation of Compound 1

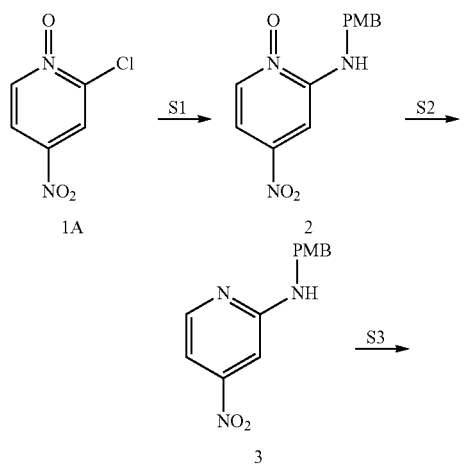

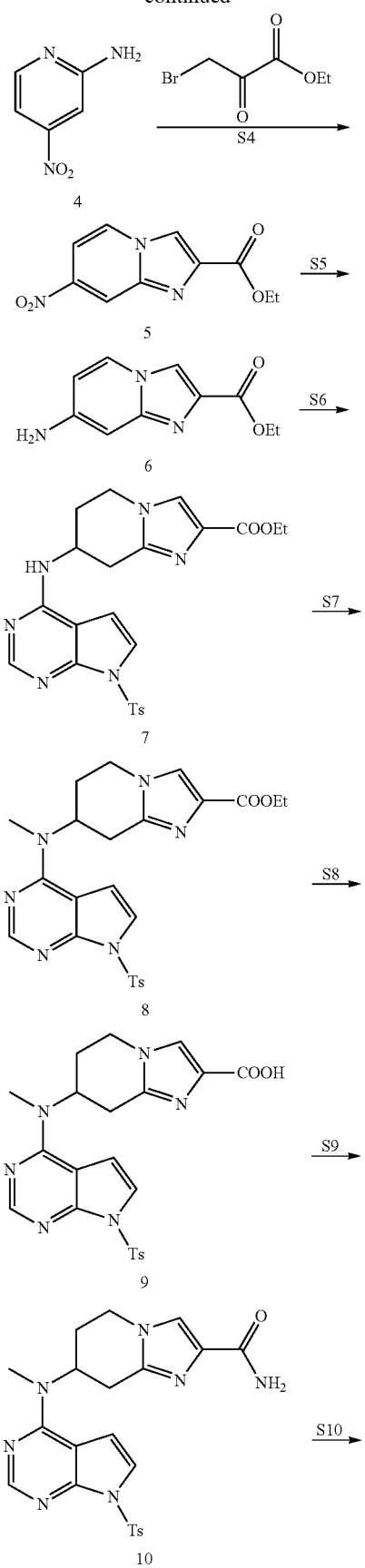

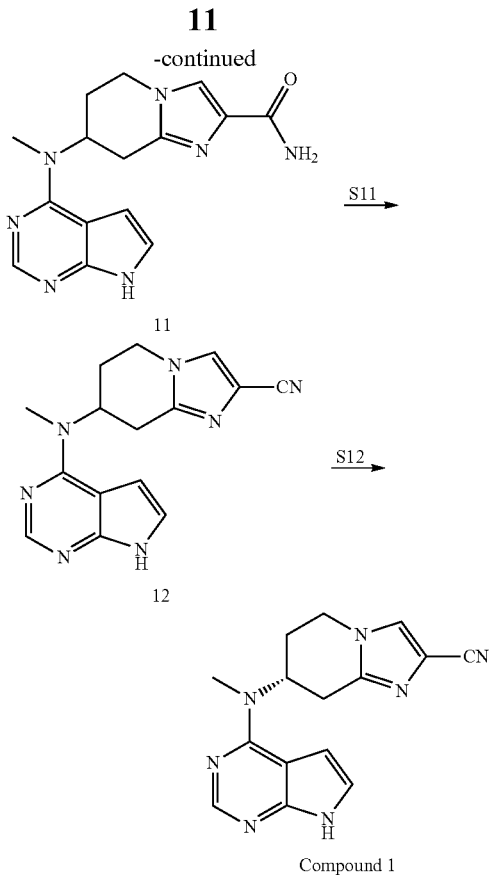

Step 1: 2-chloro-4-nitro-1-oxo-pyridin-1-ium (40.0 g, 229.2 mmol) and (4-methoxyphenyl)methylamine (63 g, 458.4 mmol) were dissolved in EtOH (400 mL), and the resulting solution was stirred at reflux for 5 hours. TLC (PE:EA=2:1) showed that the reaction was complete. The EtOH was concentrated to half of its volume and was cooled in an ice bath for 2-3 hours. The resulting cold mixture was filtered, and the isolated solid was washed with PE (60 mL*3) and ice water (60 mL*3), respectively. Drying in vacuum given an orange solid, N-[(4-methoxyphenyl)methyl]-4-nitro-1-oxo-pyridin-1-ium-2-amine (2) (38.6 g, 140.2 mmol, with a yield of 61.2%). MS (ESI) calcd. For r $C_{13}H_{13}N_3O_4$ [M+H]$^+$ 275, found 276.

Step 2: to a solution of N-[(4-methoxyphenyl)methyl]-4-nitro-1-oxo-pyridin-1-ium-2-amine (5.0 g, 18.16 mmol) in CHCl$_3$ (50 mL) was dropwise added PCl$_3$ (8.4 g, 60.8 mmol) at 0° C. After the addition, the reaction mixture was heated to 25° C. and stirred vigorously for 16 hours. TLC (PE:EA=1:1) showed that the reaction was complete. The reaction mixture was filtered, and the resulting solid was washed with PE (30 mL*3) to give a yellow solid compound, N-[(4-methoxyphenyl)methyl]-4-nitro-pyridin-2-amine (3) (4.2 g, a crude product) which was directly used in the next step without further purification. MS (ESI) calcd. For $C_{15}H_{18}N_6$ [M+H]$^+$259, found 260.

Step 3: to a solution of N-[(4-methoxyphenyl)methyl]-4-nitro-pyridin-2-amine (4.2 g, 16.2 mmol) in toluene (10 mL) was dropwise added TFA (5.0 mL) at atmospheric temperature. Then, the mixture was stirred at 80° C. for 2 hours. TLC (PE:EA=1:1) showed that the reaction was complete. The mixture was concentrated under reduced pressure to remove the solvent. The residue was diluted with H$_2$O (50 mL), and its pH was adjusted to be neutral with solid NaHCO$_3$. The aqueous phase was extracted with EA (50 mLE*3). The combined organic phase was dried over anhydrous sodium sulfate, filtered, and concentrated under reduced pressure. The resulting residue was purified by column chromatography (silica, petroleum ether/ethyl acetate=1/0-1:1) to obtain an orange solid compound, 4-nitropyridine-2-amine (4) (700 mg, 5.0 mmol, with a yield of 31.1%). MS (ESI) calcd. For $C_5H_5N_3O_2$ [M+H]$^+$ 139, found 140.

Step 4: to a solution of 4-nitropyridine-2-amine (200 mg, 1.4 mmol) in DME (5 mL) was added 3-bromo-2-oxo-propanoate (280 mg, 1.4 mmol) at atmospheric temperature. The resulting mixture was stirred at 25° C. for 1 hour, and then was concentrated under reduced pressure to remove the solvent. The residue was dissolved with EtOH (10 mL); and then was refluxed for 3 hours. TLC showed that the reaction was complete. The reaction solution was cooled to room temperature, and the solvent was concentrated under reduced pressure. The residue was basified with saturated NaHCO$_3$ aqueous solution (25 mL). The aqueous phase was extracted with DCM (15 mL*3); and the combined organic phase was dried over anhydrous sodium sulfate, filtered, and concentrated under reduced pressure. The resulting residue was purified by flash column chromatography (EA:PE=10-60%) to obtain a light yellow solid compound, ethyl 7-nitroimidazo[1,2-]pyridin-2-carboxylate (5) (302 mg, with a yield of 88.9%). MS (ESI) calcd. For $C_{10}H_9N_3O_4$ [M+H]$^+$ 235, found 236.

Step 5: a solution of ethyl 7-nitroimidazo[1,2-a]pyridin-2-carboxylate (150 mg, 637.8 mmol) in ethanol (20 mL) was added HCl (7 mg, 0.2 mmol) and PtO$_2$ (15 mg, 0.6 mmol) at atmospheric temperature. The reaction system was repeatedly vacuumed and filled with N$_2$ for three times, then filled with H$_2$ (50 psi), and was stirred at 50° C. for 16 hours. TLC (PE:EA=1:1) showed that the reaction was complete. The reaction mixture was concentrated to half of its volume, and filtered to obtain a white solid compound, ethyl 7-amino-5,6,7,8-tetrahydroimidazo[1,2-a]pyridin-2-carboxylate hydrochloride (6) (120 mg, a crude product). MS (ESI) calcd. For $C_{10}H_{15}N_3O_2$ [M+H]$^+$ 209, found 210.

Step 6: ethyl 7-amino-5,6,7,8-tetrahydroimidazo[1,2-a]pyridin-2-carboxylate hydrochloride (100 mg, 0.4 mmol) and 4-chloro-7-(p-toluenesulfonyl)pyrrolo[2,3-d]pyrimidine (137 mg, 0.4 mmol) were dissolved in n-BuOH (5 mL), and DIEA (158 mg, 1.2 mmol) were added to the above solution. The resulting mixture was stirred under reflux for 16 hours. LC-MS showed that the reaction was complete. The reaction mixture was concentrated under reduced pressure, and the resulting residue was diluted with H$_2$O (10 mL). The aqueous phase was extracted with EA (20 mL*3); and the combined organic phase was dried over anhydrous sodium sulfate, filtered, and concentrated under reduced pressure. The resulting residue was purified by preparative TLC (PE:EA=0:1) to obtain a light yellow solid compound, ethyl 7-[[7-(p-toluenesulfonyl) pyrrolo[2,3-d]pyrimidin-4-yl] amino]-5,6,7,8-tetrahydroimidazo[1,2-α]pyridin-2-carboxylate (7) (55 mg, 0.11 mmol, with a yield of 28.1%). MS (ESI) calcd. For $C_{23}H_{24}N_6O_4S$ [M+H]$^+$ 480, found 481.

Step 7: to a solution of ethyl 7-[[7-(p-toluenesulfonyl) pyrrolo[2,3-d]pyrimidin-4-yl]amino]-5,6,7,8-tetrahydroimidazo[1,2-α]pyridin-2-carboxylate (3.0 g, 6.2 mmol) in THF (150 mL) was added NaH (499 mg, 12.5 mmol) in portions under N$_2$ atmosphere at 0° C. The mixture was stirred at that temperature for 1 hour, and then was dropwise added MeI (7.1 g, 50.2 mmol). After the addition, the mixture was stirred at atmospheric temperature for 1 hour. TLC showed that the reaction was complete. The reaction was quenched by the addition of saturated NH$_4$Cl (10 mL), and then was diluted by the addition of ice water (50 mL). The aqueous phase was extracted with a mixed solvent of DCM/MeOH (3:1, 50 mL*3). The combined organic phase was dried over sodium sulfate, filtered, and concentrated under reduced pressure. The resulting crude product was purified by flash column chromatography (DCM:MeOH=10:1) to obtain a light yellow solid, ethyl 7-[methyl-[7-(p-toluenesulfonyl)pyrrolo[2,3-d]pyrimidin-4-yl]amino]-5,6,7,8-tetrahydroimidazo[1,2-a]pyridin-2-carboxylate (8) (1.5 g, with a yield of 45%). MS (ESI) calcd. For $C_{24}H_{26}N_6O_4S$ [M+H]$^+$ 494, found 495.

Step 8: to a solution of 7-[methyl-[7-(p-toluenesulfonyl)pyrrolo[2,3-d]pyrimidin-4-yl]amino]-5,6,7,8-tetrahydroimidazo[1,2-a]pyridin-2-carboxylate (4.0 g, 8.1 mmol) in THF (40 mL) and $H_2O$ (8 mL) was added LiOH.$H_2O$ (509 mg, 12.1 mmol), and the mixture was stirred at 20° C. for 10 hours. TLC showed that the reactants were completely consumed. THF in the reaction mixture was removed under reduced pressure; and the pH of the residue was adjusted to 2-3 with 2M HCl (4 mL) to form a white solid. The solid was filtered out, and was concentrated under reduced pressure to obtain 7-[methyl-[7-(p-toluenesulfonyl)pyrrolo[2,3-d]pyrimidin-4-yl]amino]-5,6,7,8-tetrahydroimidazo[1, 2-a]pyridin-2-carboxylic acid (9) as a white solid (3.6 g, with a yield of 95.4%). MS (ESI) calcd. For $C_{22}H_{22}N_6O_4S$ [M+H]$^+$ 466, found 467.

Step 9: to a solution of 7-[methyl-[7-(p-toluenesulfonyl)pyrrolo[2,3-d]pyrimidin-4-yl]amino]-5,6,7,8-tetrahydroimidazo[1, 2-a]pyridin-2-carboxylic acid (1.8 g, 3.9 mmol) in DMF (20 mL) was added CDI (751 mg, 4.6 mmol) at 0° C. The reaction solution was heated to 25° C. and stirred for 2 hours, and after that, solid ammonium chloride (2.1 g, 38.6 mmol) was added, and then the reaction was kept overnight at atmospheric temperature. LC-MS showed that the reactants were completely consumed. The reaction mixture was poured into ice water (50 mL), and a white solid was precipitated. The solid was filtered out, washed with water (20 mL), and was dried under reduced pressure in a rotating manner to obtain 7-[methyl-[7-(p-toluenesulfonyl)pyrrolo[2,3-d]pyrimidin-4-yl]amino]-5,6,7,8-tetrahydroimidazo[1, 2-a]pyridin-2-carboxamide (10) as a white solid (2.5 g, a crude product) which product was directly used in the next step. MS (ESI) calcd. For $C_{22}H_{23}N_7O_3S$ [M+H]$^+$ 465, found 466.

Step 10: 7-[methyl-[7-(p-toluenesulfonyl)pyrrolo[2,3-d]pyrimidin-4-yl]amino]-5,6,7,8-tetrahydroimidazo[1, 2-a]pyridin-2-carboxamide (2.5 g, 5.4 mmol) was dissolved in a mixture of THF (20 mL), MeOH (10 mL) and $H_2O$ (6 mL), and NaOH (429.6 mg, 10.7 mmol) was added. The mixture was heated to 60° C. and stirred for 30 minutes. LC-MS showed that the reactants were completely consumed. The reaction mixture was concentrated under reduced pressure to obtain 7-[methyl-[heptahydropyrrolo[2,3-d]pyrimidin-4-yl]amino]-5,6,7,8-tetrahydroimidazo[1,2-α]pyridin-2-carboxamide (11) as a white solid (2.5 g, a crude product) which was directly used in the next step. MS (ESI) calcd. For $C_{15}H_{17}N_7O$ [M+H]$^+$ 311, found 312.

Step 11: to a solution of 7-[methyl-[heptahydropyrrolo[2,3-d]pyrimidin-4-yl]amino]-5,6,7,8-tetrahydroimidazo[1,2-a]pyridin-2-carboxamide (2.0 g, 6.4 mmol) and triethylamine (3.9 g, 38.5 mmol) in THF (20 mL) was dropwise added TFAA (4.1 g, 19.3 mmol) at 0° C. After the addition, the reaction solution was stirred at atmospheric temperature for 30 minutes. LC-MS showed the starting materials were completely consumed. The reaction mixture was poured into ice water (20 mL), and extracted with DCM/MeOH (5:1, 100 mL*2). The combined organic layer was washed with saturated saline (20 mL), dried over anhydrous sodium sulfate, filtered, and concentrated under reduced pressure to obtain a residue. The residue was purified by column chromatography (DCM/MeOH=40/1 to 20:1) to obtain 7-[methyl-[7-hydropyrrolo[2,3-d]pyrimidin-4-yl]amino]-5,6,7,8-tetrahydroimidazo[1,2-a]pyridin-2-nitrile (12,378 mg, with a yield of 19.8%). MS (ESI) calcd. For $C_{15}H_{15}N_7$ [M+H]$^+$ 293, found 294. 1H NMR (400 MHz, DMSO-d6) 11.44-11.71 (m, 1H), 7.99-8.17 (m, 2H), 7.11-7.20 (m, 1H), 6.63 (dd, J=1.76, 3.26 Hz, 1H), 5.33 (br. s., 1H), 4.21-4.21-4.31 (m, 1H), 4.13 (dt, J=4.14, 12.49 Hz, 1H), 3.27 (s, 3H), 2.91-3.11 (m, 2H), 2.31-2.44 (m, 1H), 2.07 (d, J=11.54 Hz, 1H).

Step 12: racemic 7-[methyl-[7-hydropyrrolo[2,3-d]pyrimidin-4-yl]amino]-5,6,7,8-tetrahydroimidazo[1,2-a]pyridin-2-nitrile (30 mg, 102.3 umol) was separated by a chiral column to obtain the compound 1 (10 mg, with a yield of 32.8%).

The conditions for SFC (supercritical fluid chromatography) separation:

Column: AD (250 mm*30 mm, 10 um) chiral column;
Mobile phase: A: supercritical $CO_2$, B: ethanol (containing 0.1% isopropanol), A:B=55:45;
Flow rate: 80 mL/min;
Column temperature: 38° C.;
Wave length: 220 nm;
Injection pressure: 100 Bar;
Nozzle temperature: 60° C.;
Evaporation temperature: 20° C.; and
Reconditioning temperature: 25° C.

Compound 1: retention time 6.407 min; MS (ESI) calcd. For $C_{15}H_{15}N_7$ [293, found 294 M+H]+. Purity 98.8%, e.e. was 98.9%; $[\alpha]_D^{20}$=+78.4° (c=0.6, DMSO). MS ESI calcd. For $C_{15}H_{15}N_7$ [M+H]$^+$ 294, found 294. $^1$H NMR (400 MHz, DMSO-d6) δ ppm 2.02-2.15 (m, 1H) 2.39 (qd, J=12.42, 5.90 Hz, 1H) 2.92-3.12 (m, 2H) 3.28 (s, 3H) 4.05-4.36 (m, 2H) 5.20-5.45 (m, 1H) 6.64 (dd, J=3.39, 1.88 Hz, 1H) 7.17 (dd, J=3.26, 2.51 Hz, 1H) 8.02-8.17 (m, 2H) 11.69 (br s, 1H).

Example 2: Preparation of Crystal Form F of Compound 3 and Crystal Form A of Compound 1

1 g of the compound 1 was added to 5 mL of acetone and 0.5 mL of TFA, and was heated to reflux. 10 mL of MTBE was added. The mixture was filtered to remove insoluble substances. The resulting solution was allowed to stand for 12 h to precipitate a solid which was filtered out. The filter cake was washed with MTBE and dried to obtain a trifluoroacetate salt of the compound 1, namely, the crystal form F of the compound 3. After each gram of the compound 3 was dissolved by adding 10 mL water, 0.1 mL TFA and 1 mL MeOH, the system was adjusted to be alkaline with a saturated $NaHCO_3$ solution. At this time, a white solid was precipitated and filtered. The filter cake was washed with $H_2O$ (5 mLE*3) to remove inorganic salts. Drying in vacuum given a free white solid, namely the crystal form A of the compound 1.

Example 3: Preparation of Crystal Form B of Compound 1

About 20 mg of the crystal form A of the compound 1 was added to 20 mL of ethanol, and the mixture was dissolved with the help of sonication, and then was centrifuged. The resulting supernatant was naturally volatilized in a fume hood. The residual solid sample was dried in a vacuum drying oven (30° C.) overnight to obtain the crystal form B of the compound 1.

Example 4: Preparation of Crystal Form C of Compound 1

About 20 mg of the crystal form A of the compound 1 was added to 20 mL of tetrahydrofuran, and the mixture was dissolved with the help of sonication, and then was centrifuged. The resulting supernatant was naturally volatilized in a fume hood. The residual solid sample was dried in a vacuum drying oven (30° C.) overnight to obtain the crystal form C of the compound 1.

Example 5: Preparation of Crystal Form D of Compound 1

About 25 mg of the crystal form A of the compound 1 was dropwise added to 10 mL of a solvent mixture of ethanol-water (3:1), and the mixture was placed on a magnetic stirrer and heated (50° C.) for dissolution, and was rapidly filtered while being ho. The filtrate was cooled in the refrigerator at 5° C. The precipitated solid sample was dried in a vacuum drying oven (30° C.) overnight to obtain the crystal form D of the compound 1.

Example: 6: Preparation of Compound 2

60 mg of the compound 1 was added to a glass vial, followed by 2 mL of DMSO. The mixture was placed on a magnetic stirrer and heated (50° C.) for dissolution, and then p-toluenesulfonic acid (the molar ratio of the compound 1 to p-toluenesulfonic acid was 1:1) was slowly added. It was observed that all samples were in a solution state and no precipitation was generated. After heating and stirring for 1 hour, heating was stopped; and the sample solution was naturally cooled while stirring was continued. After 3 hours, the sample was still in a solution state, and ethyl acetate was added. The solution was concentrated by rotary evaporation, and then was freeze-dried to obtain the compound 2.

Example 7: Preparation of Crystal Form E of Compound 2

About 40 mg of the original compound 2 was added to 0.4 mL of methanol to form a suspension. The suspension sample was shaken on a thermostatic homogenizer (40° C.) for 2 days (away from light). The residual solid was centrifuged and dried overnight in a vacuum drying oven at 25° C. to obtain the crystal form E of the compound 2.

Experimental Example 1: Solubility Tests of Crystal Form A of Compound 1 in Different Solvents These solubility tests were carried out by manually stepwise dilution and simultaneous observation of dissolution at atmospheric temperature. About 2 mg of the crystal form A of the compound 1 was added to vials having a different liquid phase respectively, and then a small amount of an organic solvent or solvent mixture (shown in Table 7) was added repeatedly. The dissolution of the crystal form A of the compound 1 was observed. The test results were shown in Table 7.

TABLE 7

Solubility of Form A in Different Solvents

| NO. | Solvent | Solubility (mg/mL) | Conclusion |
|---|---|---|---|
| 1 | Methanol | <2 | Slightly soluble/very slightly soluble |
| 2 | Ethanol | <2 | Slightly soluble/very slightly soluble |
| 3 | Isopropanol | <2 | Slightly soluble/very slightly soluble |
| 4 | N-butanol | <2 | Slightly soluble/very slightly soluble |
| 5 | Acetonitrile | <2 | Slightly soluble/very slightly soluble |
| 6 | Acetone | <2 | Slightly soluble/very slightly soluble |
| 7 | Methyl ethyl ketone | <2 | Slightly soluble/very slightly soluble |
| 8 | Methyl isobutyl ketone | <2 | Slightly soluble/very slightly soluble |
| 9 | Ethyl acetate | <2 | Slightly soluble/very slightly soluble |
| 10 | Isopropyl acetate | <2 | Slightly soluble/very slightly soluble |
| 11 | Methyl tert-butyl ether | <2 | Slightly soluble/very slightly soluble |
| 12 | Tetrahydrofuran | <2 | Slightly soluble/very slightly soluble |
| 13 | 2-methyltetrahydrofuran | <2 | Slightly soluble/very slightly soluble |
| 14 | Toluene | <2 | Slightly soluble/very slightly soluble |
| 15 | Heptane | <2 | Slightly soluble/very slightly soluble |
| 16 | Cyclohexane | <2 | Slightly soluble/very slightly soluble |
| 17 | 1,4-dioxane | <2 | Slightly soluble/very slightly soluble |
| 18 | Water | <2 | Slightly soluble/very slightly soluble |
| 19 | Methanol-water (1:1) | <2 | Slightly soluble/very slightly soluble |
| 20 | Methanol-water (3:1) | <2 | Slightly soluble/very slightly soluble |
| 21 | Ethanol-water (1:1) | <2 | Slightly soluble/very slightly soluble |
| 22 | Ethanol-water (3:1) | <2 | Slightly soluble/very slightly soluble |
| 23 | Acetonitrile-water (1:1) | <2 | Slightly soluble/very slightly soluble |
| 24 | Acetone-water (1:2) | <2 | Slightly soluble/very slightly soluble |
| 25 | Isopropyl alcohol-water (1:1) | <2 | Slightly soluble/very slightly soluble |

Experimental Example 2: Stability Tests of Crystal Form a of Compound 1 in Different Solvents 30 mg of the crystal form A of the compound 1 was added to 0.2 mL of a single or mixed solvent in the table below, respectively; and each mixture was stirred at 40° C. for 2 days and centrifuged. The solids in all samples were collected and dried overnight in a vacuum drying oven (25° C.). Crystal forms of the solids were detected by XRPD and the results were shown in Table 8.

TABLE 8

Stability Tests of Crystal Form A of Compound 1 in Different Solvents

| NO. | Solvent | Appearance (2 days) | Results |
|---|---|---|---|
| 1 | Methanol | Suspension | Crystal form A |
| 2 | Ethanol | Suspension | Crystal form A |

TABLE 8-continued

Stability Tests of Crystal Form A of Compound 1 in Different Solvents

| NO. | Solvent | Appearance (2 days) | Results |
|---|---|---|---|
| 3 | Isopropanol | Suspension | Crystal form A |
| 4 | Acetone | Suspension | Crystal form A |
| 5 | Ethyl acetate | Suspension | Crystal form A |
| 6 | Tetrahydrofuran | Suspension | Crystal form A |
| 7 | Methanol-water (3:1) | Suspension | Crystal form A |
| 8 | Ethanol-water (3:1) | Suspension | Crystal form A |
| 9 | Acetone-water (1:2) | Suspension | Crystal form A |
| 10 | Isopropyl alcohol-water (1:1) | Suspension | Crystal form A |

Experimental Example 3: Solid Stability Tests of Crystal Form E of Compound 2 Under High Temperature, High Humidity and Strong Light According to the "Guidelines for the Stability Test of APIs and Preparations" (General Principles 9001 of the Four Parts of the Chinese Pharmacopoeia, 2015 Edition), the stability of the crystal form E of the compound 2 was investigated at high temperature (60° C., open), high humidity (room temperature/relative humidity 92.5%, open) and strong light radiation (5000 lx, close).

A suitable amount of the crystal form E sample of the compound 2 was placed on the bottom of a glass vial and spread into a thin layer. The vial in which the samples were placed at high temperature and high humidity was sealed with an aluminum foil, and small holes were formed in the aluminum foil to ensure that the samples were sufficiently contacted with atmospheric air; and the sample placed at strong light radiation was sealed with a threaded cap. The samples placed under different conditions were sampled and tested by XRPD on day 5 and day 10. The test results were compared with the initial test results on day 0. The test results were shown in Table 9 below.

TABLE 9

Solid Stability Tests of Crystal Form E of Compound 2

| Test conditions | Time | Appearance | XRPD |
|---|---|---|---|
| — | day 0 | White powder | Crystal form E |
| High temperature (60° C., open) | day 5 | White powder | Crystal form E |
|  | day 10 |  | Crystal form E |
| High humidity (room temperature/relative humidity 92.5%, open) | day 5 | White powder | Crystal form E |
|  | day 10 |  | Crystal form E |
| Strong light radiation (5000 lx, close) | day 5 | White powder | Crystal form E |
|  | day 10 |  | Crystal form E |

In-Vitro Activity Tests of Jak 1, Jak 2 and Jak3 Kinases

Experimental Materials

Recombinant human JAK1, JAK2, and JAK3 proteases were purchased from Life technology. LANCE Ultra ULight™-JAK-1 (Tyr1023) peptide and LANCE Eu-W1024 Anti-phosphotyrosine (PT66) both were purchased from PerkinElmer. The plates were read using a multiplex enzyme reader Envision (PerkinElmer).

Experimental Method

The test compounds were subjected to 3-fold concentration gradient dilution to afford 11 final concentrations ranging from 10 uM to 0.17 nM; two wells were formed for each concentration; and the content of DMSO in the detection reaction was 1%.

JAK1 Enzyme Reaction:

2 nM of JAK1 protein kinase, 50 nM of LANCE Ultra ULight™-JAK-1 (Tyr1023) peptide, 38 uM of ATP, 50 mM of HEPES (pH 7.5), 10 mM of $MgCl_2$, 1 mM of EGTA, 2 mM of DTT, and 0.01% of BRIJ-35 were included. The assay plate was a White Proxiplate 384-Plus plate (PerkinElmer). The reaction was performed at room temperature for 90 minutes; and the reaction system was 10 ul.

JAK2 Enzyme Reaction:

0.02 nM of JAK2 protein kinase, 50 nM of LANCE Ultra ULight™-JAK-1 (Tyr1023) peptide, 12 uM of ATP, 50 mM of HEPES (pH 7.5), 10 mM of $MgCl_2$, 1 mM of EGTA, 2 mM of DTT, and 0.01% of BRIJ-35 were included. The assay plate was a White Proxiplate 384-Plus plate (PerkinElmer). The reaction was performed at room temperature for 60 minutes; and the reaction system was 10 ul.

JAK3 Enzyme Reaction:

0.05 nM of JAK2 protein kinase, 50 nM of LANCE Ultra ULight™-JAK-1 (Tyr1023) peptide, 4 uM of ATP, 50 mM of HEPES (pH 7.5), 10 mM of $MgCl_2$, 1 mM of EGTA, 2 mM of DTT and 0.01% of BRIJ-35 were included. The assay plate was a White Proxiplate 384-Plus plate (PerkinElmer). The reaction was performed at room temperature for 90 minutes; and the reaction system was 10 ul.

Reaction Detection:

10 ul of the detection reagent was added to a reaction plate, wherein the final concentration of LANCE Eu-W1024 Anti-phosphotyrosine (PT66) was 2 nM, and the final concentration of EDTA was 10 mM. The reagents were incubated for 60 minutes at room temperature; and the plate was read with Envision instrument.

Data Analysis

The reading was converted to an inhibition rate by the following formula: (%)=(Min−Ratio)/(Max−Min)*100%. $IC_{50}$ data were measured by 4-parameter curve fitting (Model 205 in XLFIT5, iDBS). Seen Table 9 for details.

TABLE 9

| Compound | JAK1 | JAK2 |
|---|---|---|
| Compound 1 | A | B |

A ≤ 10 nM; 10 < B ≤ 100 nM.

The compound 1 had a strong inhibitory activity against JAK1 and a relatively weak inhibitory activity against JAK2, which showed that the compound 1 had a better selective inhibition for JAK.

The invention claimed is:

1. Crystal form A of the following compound 1, of which the X-ray powder diffraction pattern comprises characteristic diffraction peaks at the following 2θ angles: 12.38±0.2°, 13.34±0.2°, 15.85±0.2°, 22.09±0.2°, 23.71±0.2°, 25.38±0.2°, 26.21±0.2° and 26.81±0.2°

Compound 1

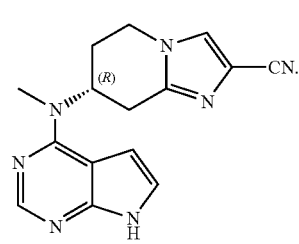

2. The crystal form A of the compound 1 of claim 1, wherein the X-ray powder diffraction (XRPD) pattern is as shown in FIG. 1.

3. Crystal form B of compound 1, of which the X-ray powder diffraction pattern comprises characteristic diffraction peaks at the following 2θ angles: 12.25±0.2°, 13.24±0.2°, 15.77±0.2°, 21.97±0.2°, 23.62±0.2°, 25.24±0.2°, 26.70±0.2° and 37.51±0.2°;

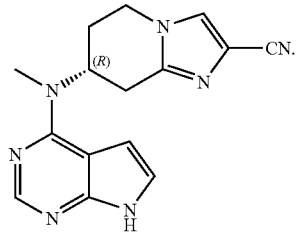

Compound 1

Figure 4:
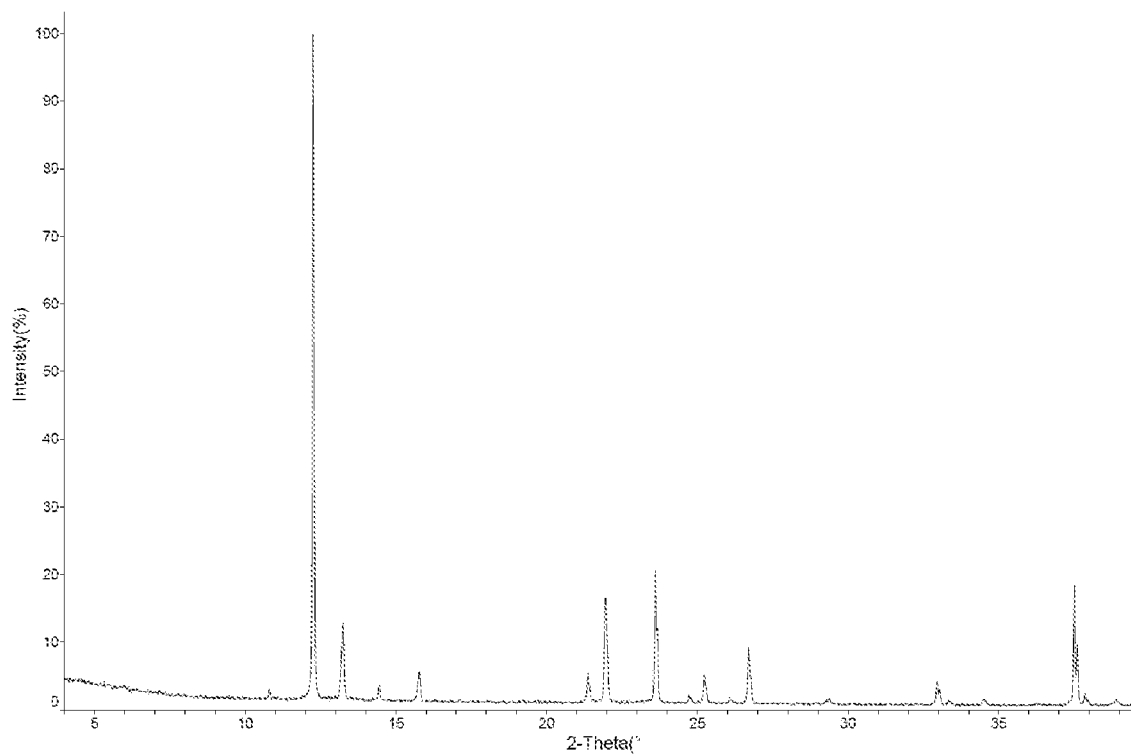
FIG. 4 is an XRPD pattern of Cu-kα radiation of the crystal form B of the compound 1.
Figure 5:
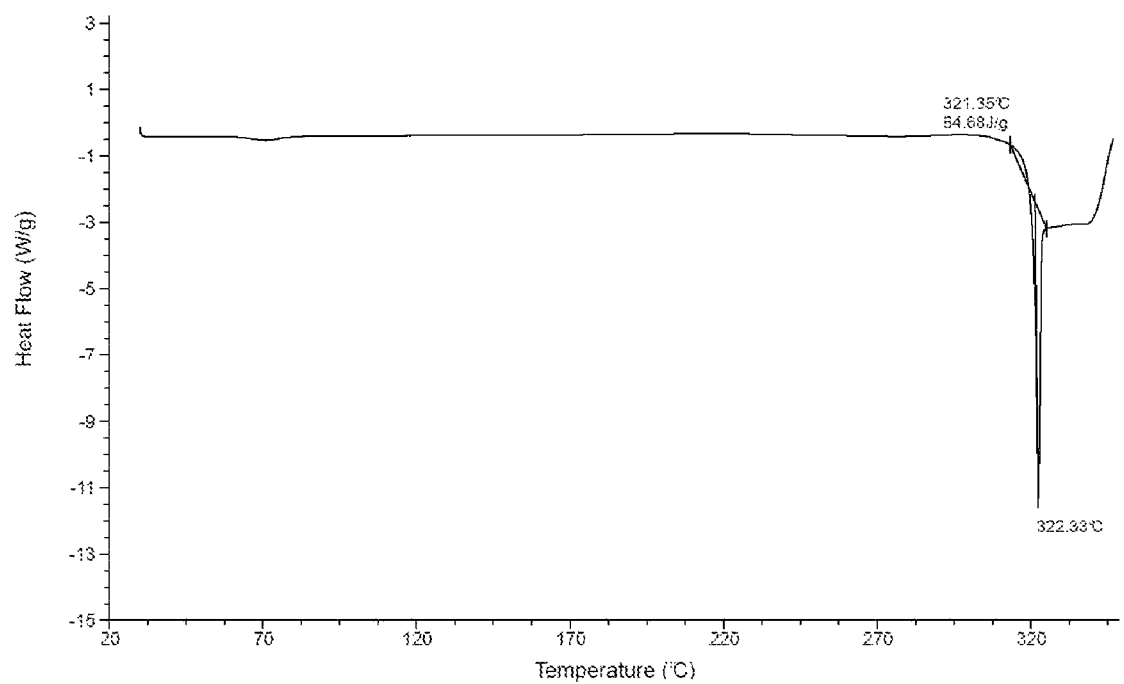
FIG. 5 is a DSC pattern of the crystal form B of the compound 1.
Figure 6:
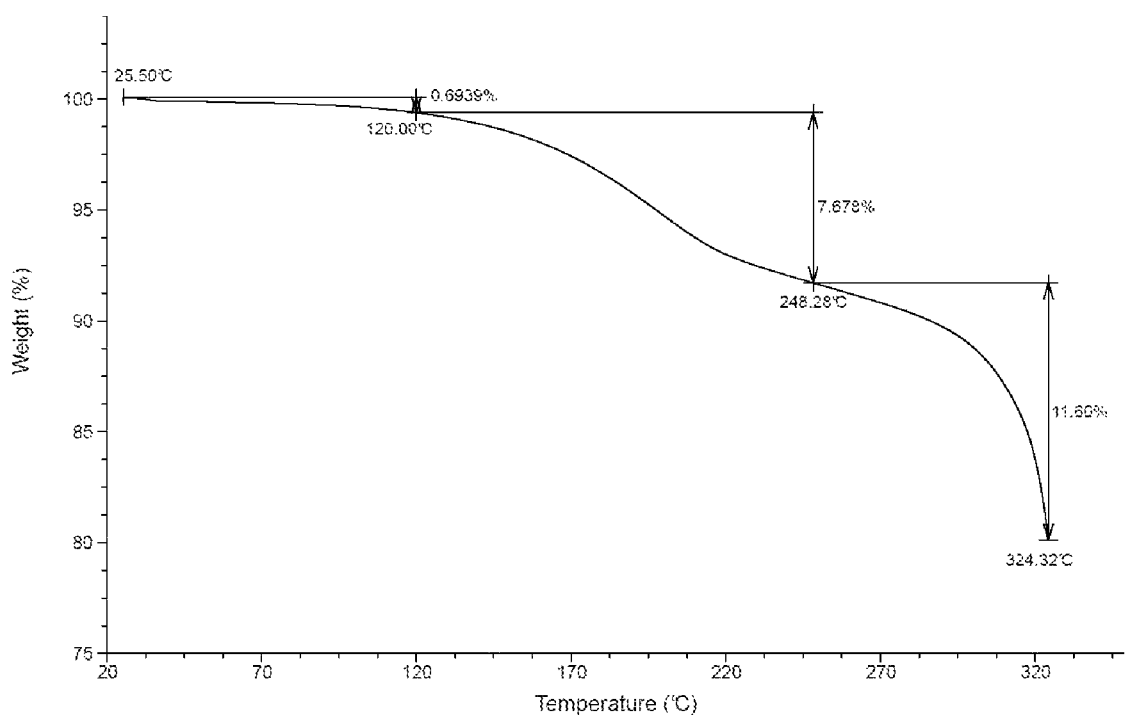
FIG. 6 is a TGA pattern of the crystal form B of the compound 1.

4. The crystal form B of the compound 1 of claim 3, wherein the XRPD pattern is as shown in FIG. 4.

5. Crystal form C of compound 1, of which the X-ray powder diffraction pattern comprises characteristic diffraction peaks at the following 2θ angles: 12.40±0.2°, 13.37±0.2°, 21.51±0.2°, 22.14±0.2°, 24.87±0.2°, 25.40±0.2° and 37.65±0.2°;

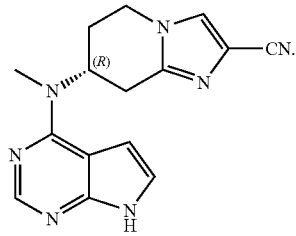

Compound 1

Figure 7:
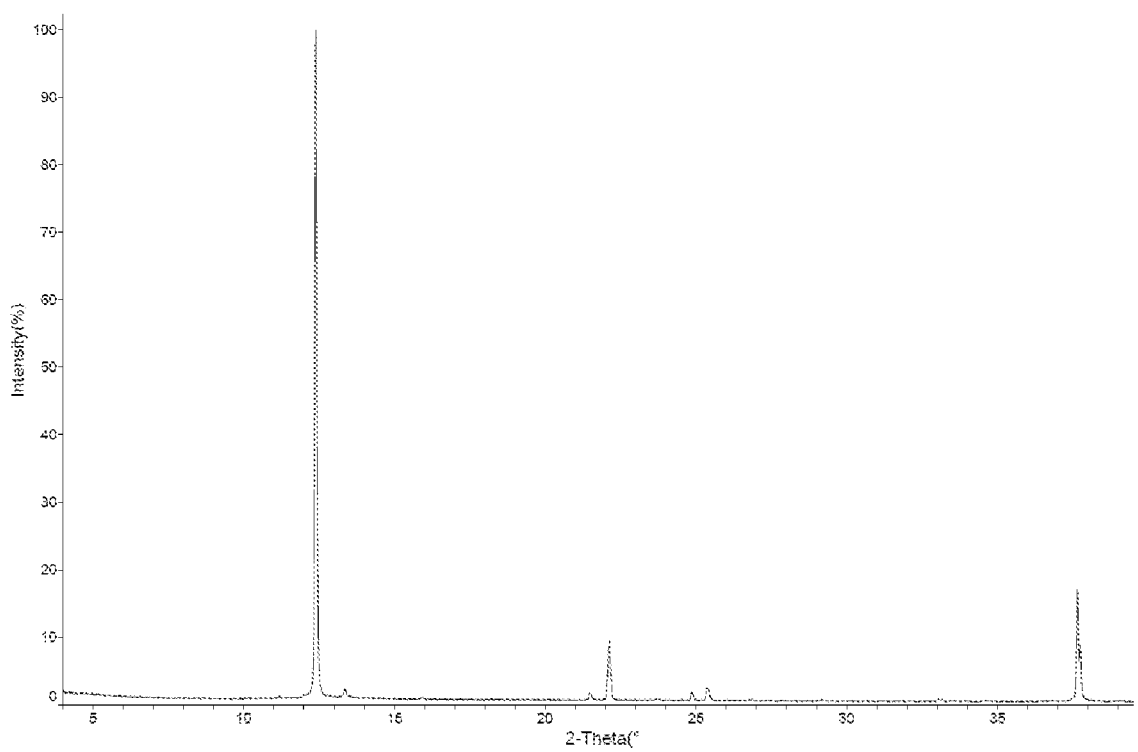
FIG. 7 is an XRPD pattern of Cu-kα radiation of the crystal form C of the compound 1.
Figure 8:
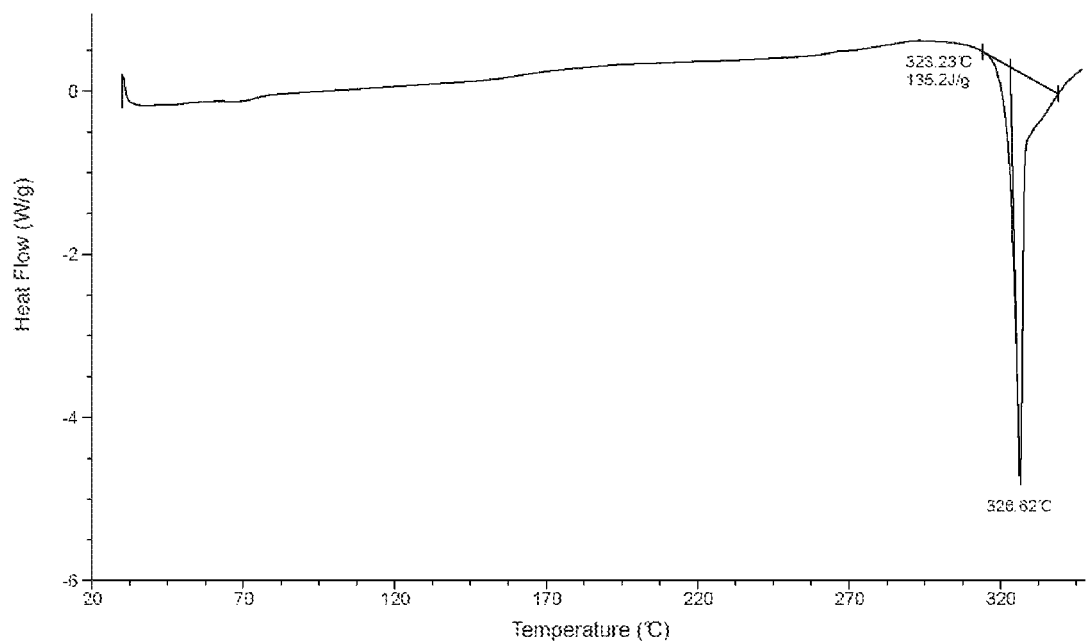
FIG. 8 is a DSC pattern of the crystal form C of the compound 1.
Figure 9:
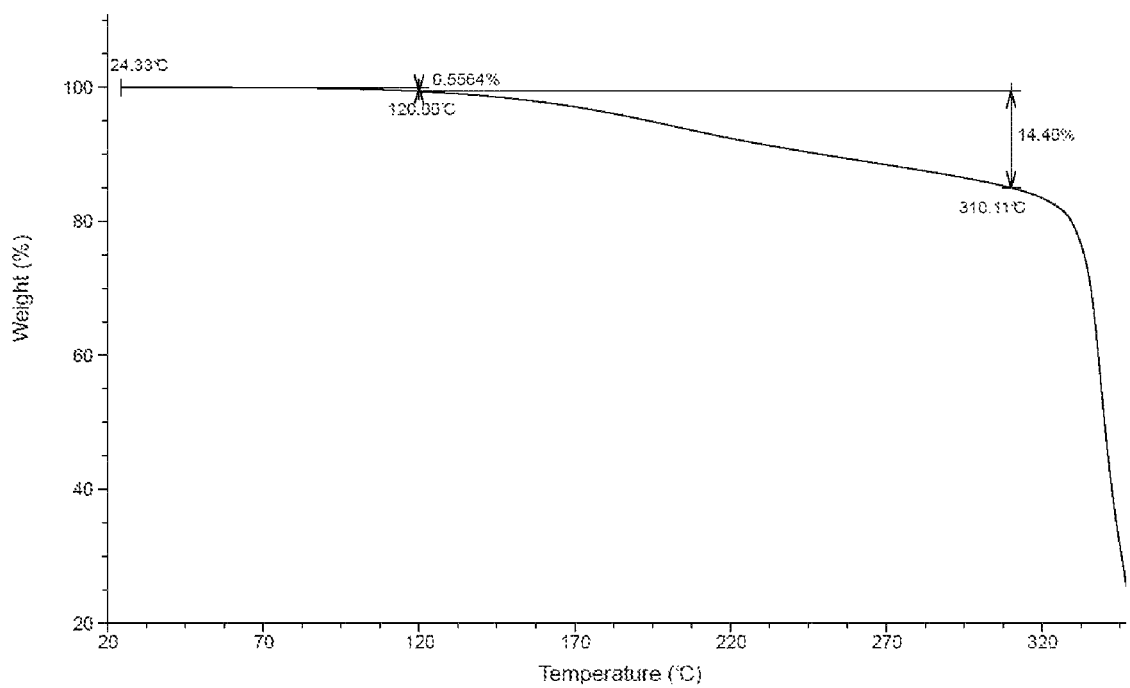
FIG. 9 is a TGA pattern of the crystal form C of the compound 1.
Figure 10:
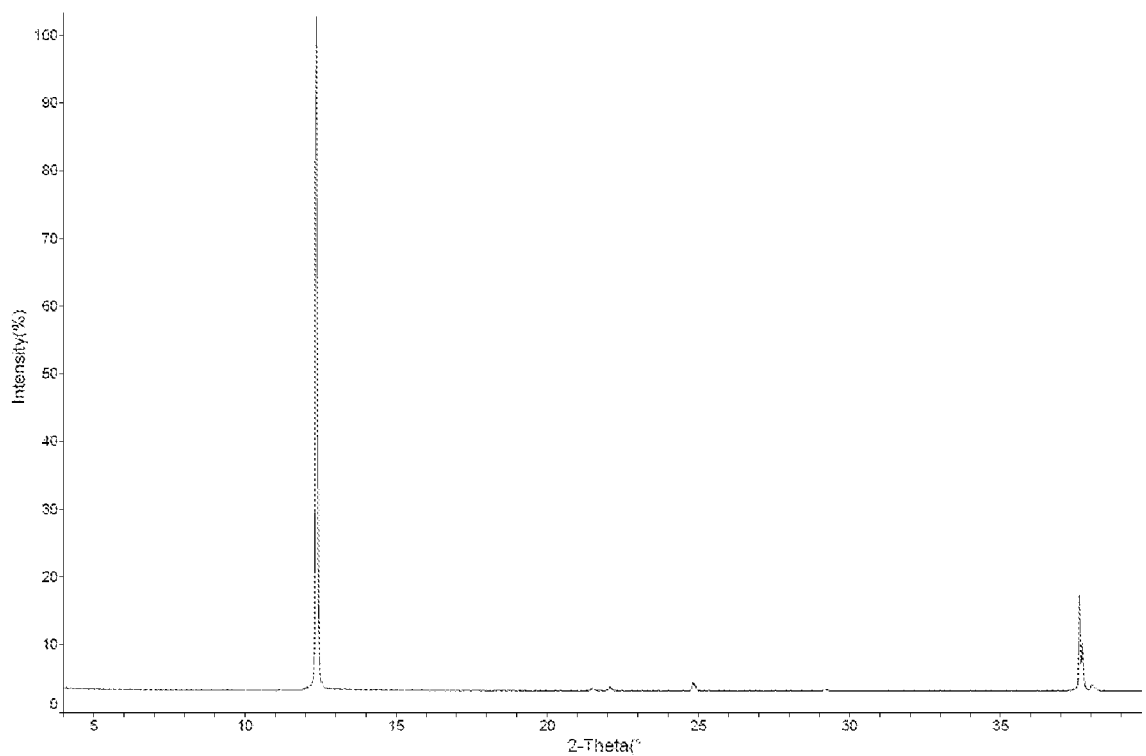
FIG. 10 is an XRPD pattern of Cu-kα radiation of the crystal form D of the compound 1.
Figure 11:
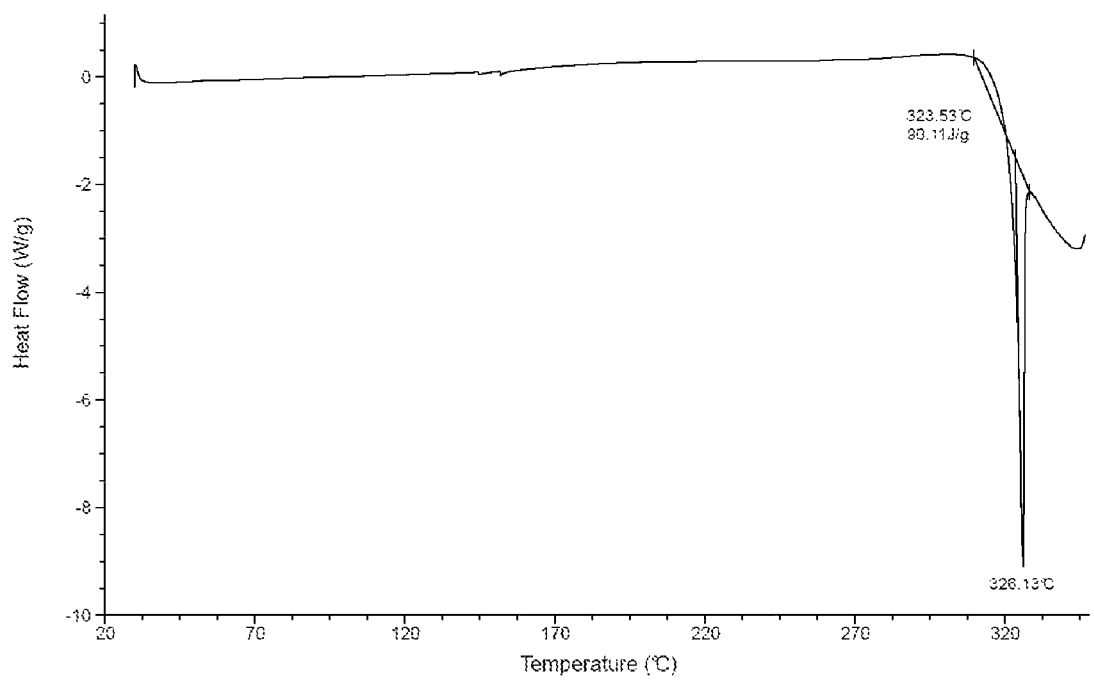
FIG. 11 is a DSC pattern of the crystal form D of the compound 1.
Figure 12:
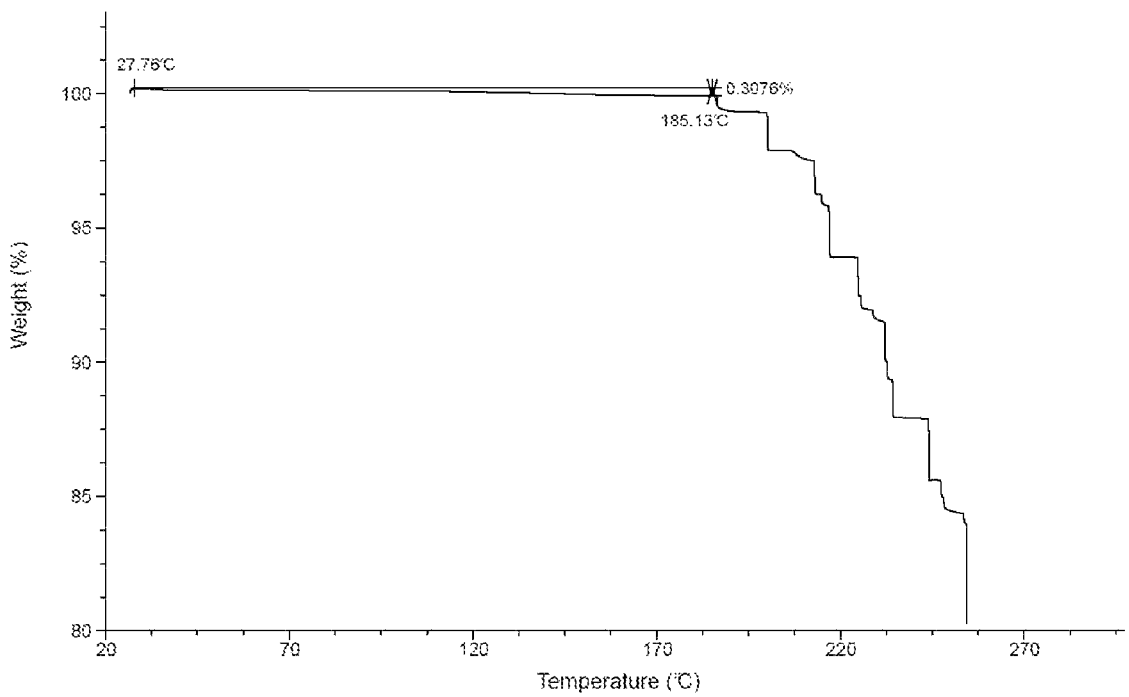
FIG. 12 is a TGA pattern of the crystal form D of the compound 1.

6. The crystal form C of the compound 1 of claim 5, wherein the XRPD pattern is as shown in FIG. 7.

7. Crystal form E of compound 2, of which the X-ray powder diffraction pattern comprises characteristic diffraction peaks at the following 2θ angles: 6.21±0.2°, 10.92±0.2°, 12.34±0.2°, 12.78±0.2°, 15.16±0.2°, 20.23±0.2°, 22.77±0.2° and 23.03±0.2°, wherein the compound 2 is a p-toluene sulfonate salt of compound 1:

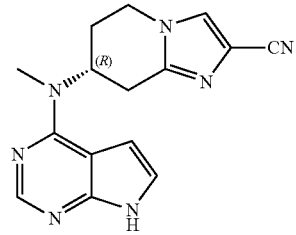

Compound 1

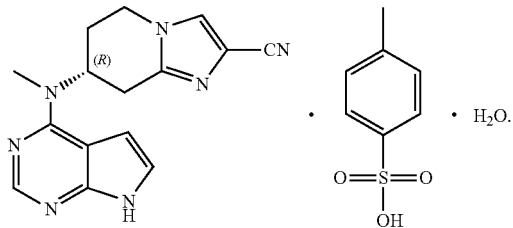

Compound 2

Figure 13:
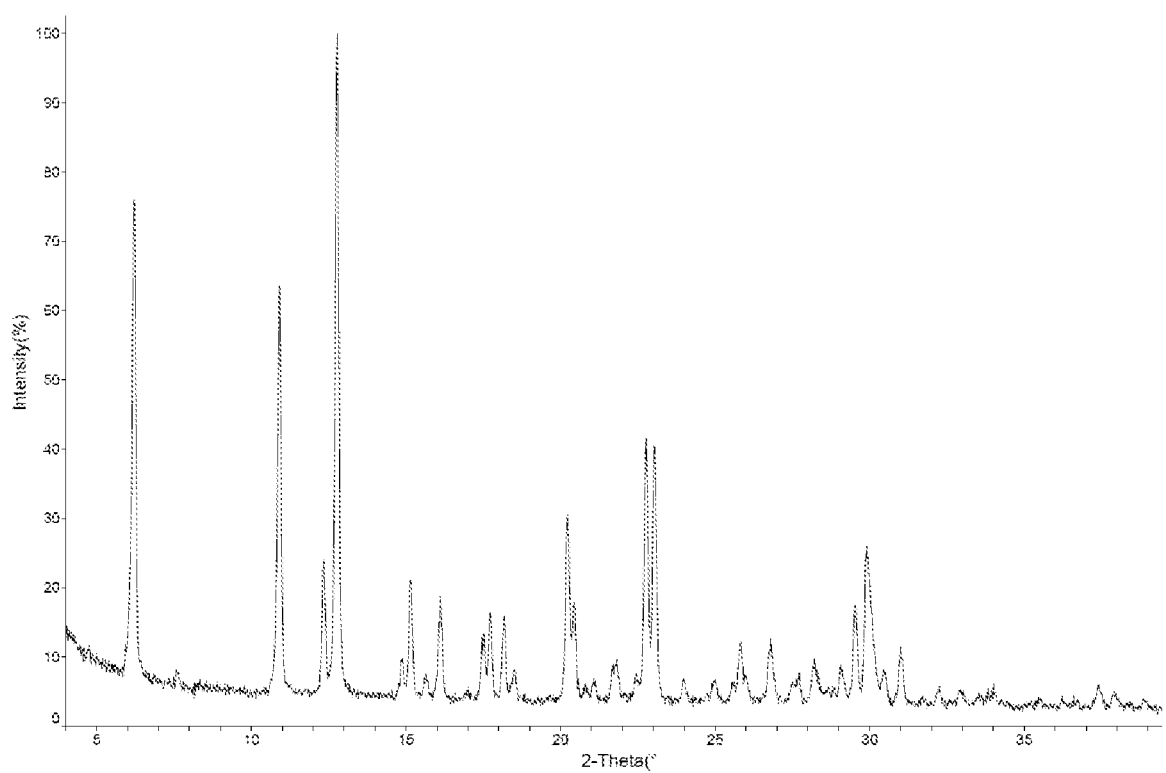
FIG. 13 is an XRPD pattern of Cu-kα radiation of the crystal form E of the compound 2.
Figure 14:
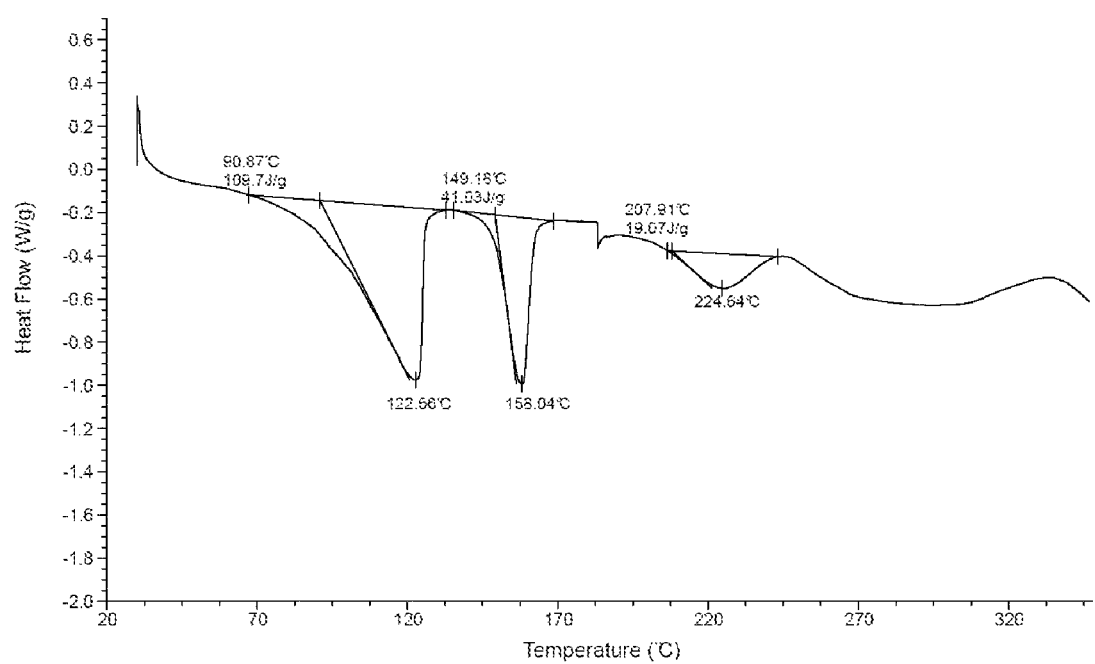
FIG. 14 is a DSC pattern of the crystal form E of the compound 2.
Figure 15:
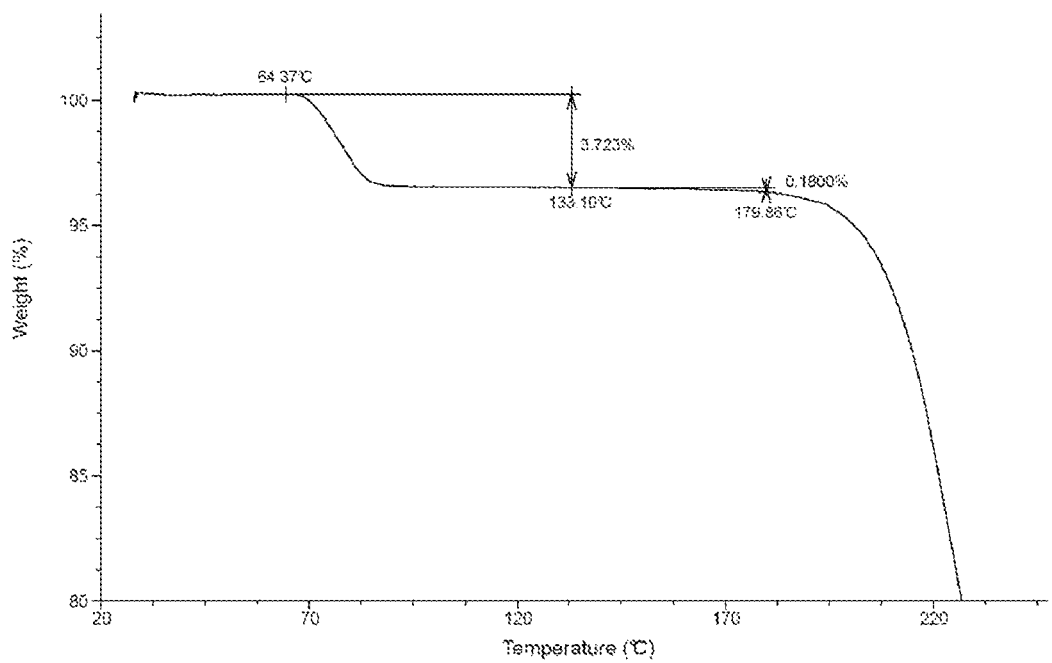
FIG. 15 is a TGA pattern of the crystal form E of the compound 2.

8. The crystal form E of the compound 2 of claim 7, wherein the XRPD pattern is as shown in FIG. 13.

9. Crystal form F of compound 3, of which the X-ray powder diffraction pattern comprises characteristic diffraction peaks at the following 2θ angles: 12.89±0.2°, 15.78±0.2°, 17.67±0.2°, 18.79±0.2°, 19.38±0.2°, 20.47±0.2°, 24.70±0.2° and 25.66±0.2°, wherein the compound 3 is a trifluoroacetate salt of compound 1:

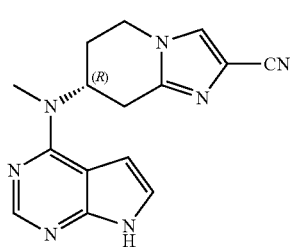

Compound 1

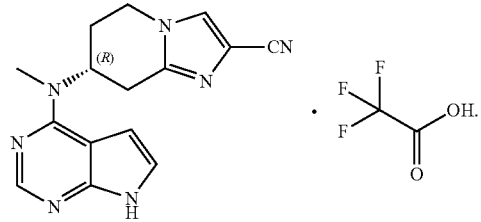

Compound 3

Figure 16:
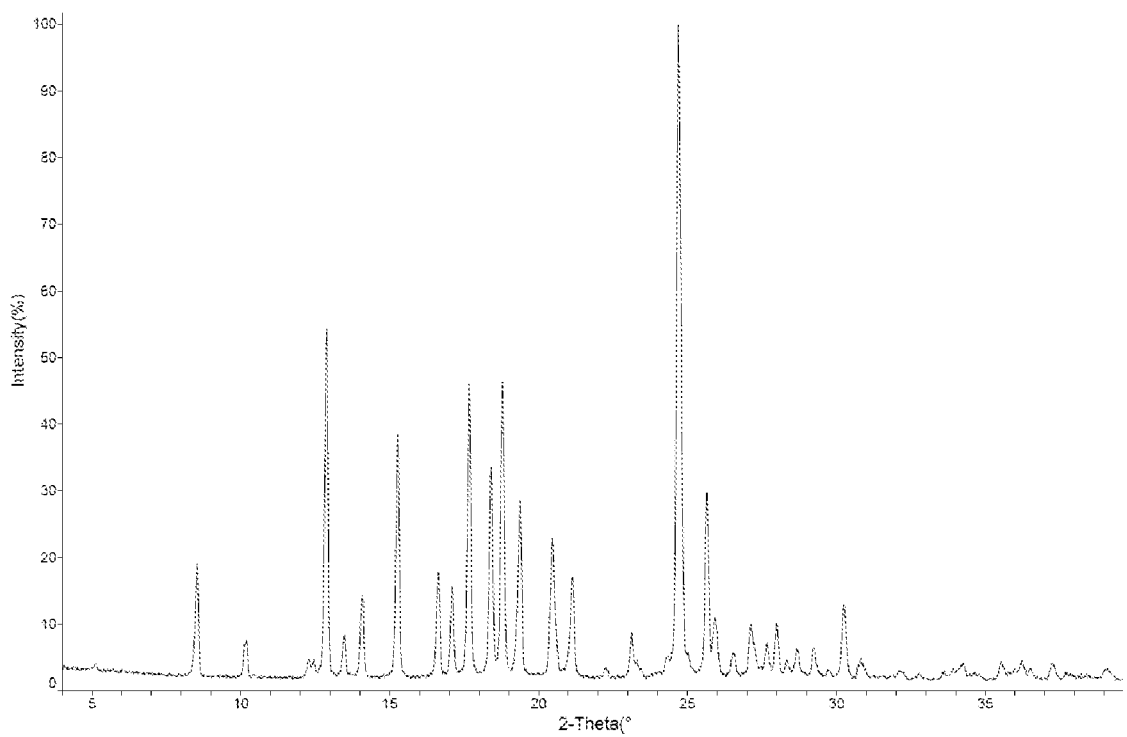
FIG. 16 is an XRPD pattern of Cu-kα radiation of the crystal form F of the compound 3.
Figure 17:
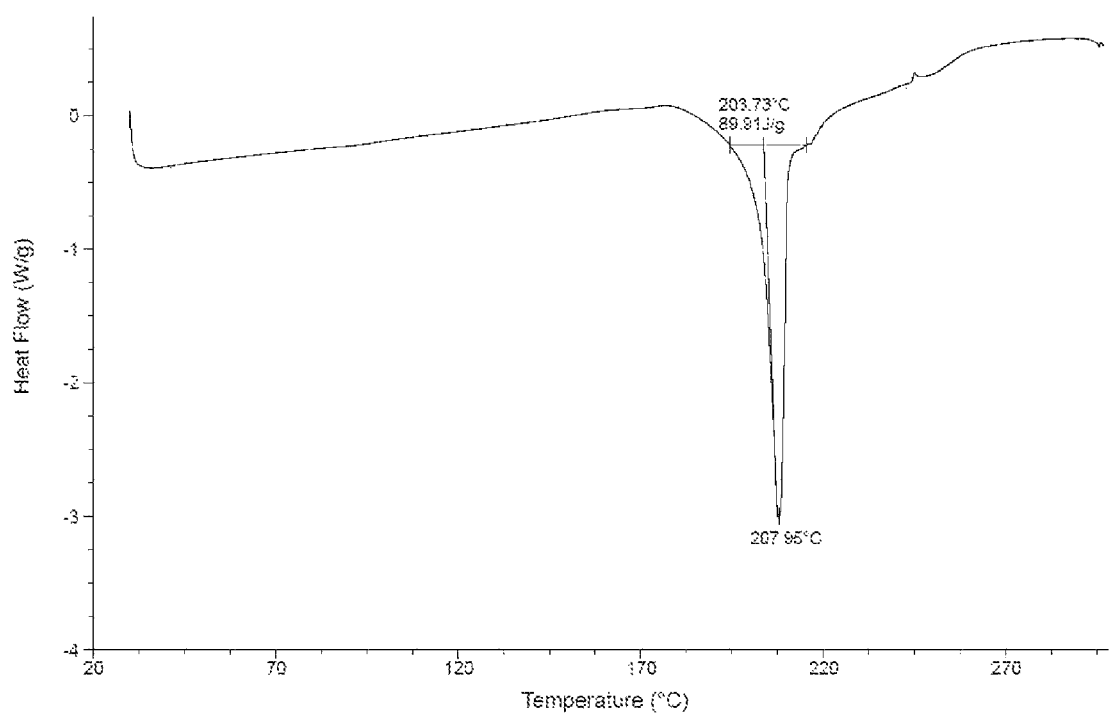
FIG. 17 is a DSC pattern of the f crystal form F of the compound 3.
Figure 18:
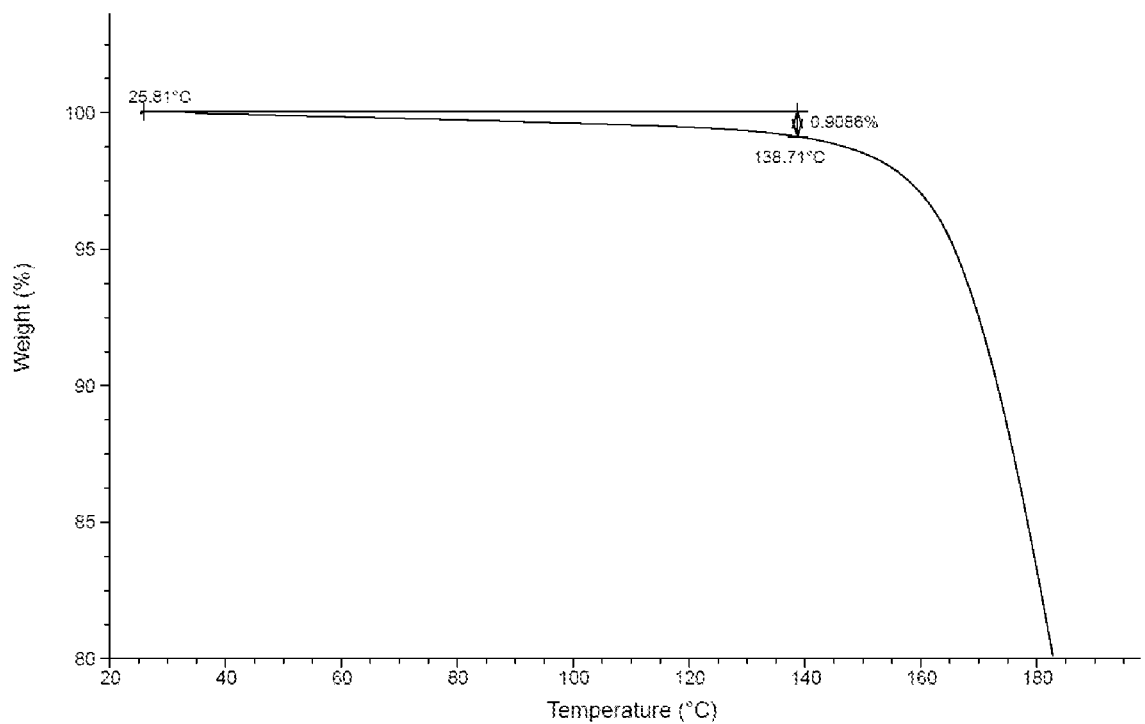
FIG. 18 is a TGA pattern of the crystal form F of the compound 3.

10. The crystal form F of the compound 3 of claim 9, wherein the XRPD pattern is as shown in FIG. 16.

* * * * *